United States Patent
Matsushima et al.

(10) Patent No.: US 7,563,950 B2
(45) Date of Patent: Jul. 21, 2009

(54) HERBICIDAL COMPOUND RESISTANT PLANT

(75) Inventors: Yutaka Matsushima, Kobe (JP); Akitsu Nagasawa, Kobe (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 70 days.

(21) Appl. No.: 11/130,391

(22) Filed: May 17, 2005

(65) Prior Publication Data
US 2006/0005268 A1 Jan. 5, 2006

(30) Foreign Application Priority Data
May 18, 2004 (JP) .............................. 2004-147363
Mar. 14, 2005 (JP) .............................. 2005-070980

(51) Int. Cl.
*C12N 15/82* (2006.01)
(52) U.S. Cl. ........................................ 800/300; 800/288
(58) Field of Classification Search .................. None
See application file for complete search history.

(56) References Cited
U.S. PATENT DOCUMENTS

| 5,179,013 | A | 1/1993 | Matsuoka et al. |
| 5,212,296 | A | 5/1993 | Dean et al. |
| 5,349,127 | A | 9/1994 | Dean et al. |
| 5,767,373 | A | 6/1998 | Ward et al. |
| 5,939,602 | A | 8/1999 | Volrath et al. |
| 6,613,961 | B1 | 9/2003 | Ohkawa et al. |
| 2002/0004457 | A1 | 1/2002 | Nevill et al. |
| 2004/0242423 | A1 | 12/2004 | Howard |
| 2005/0084859 | A1* | 4/2005 | Nakajima et al. ............... 435/6 |

FOREIGN PATENT DOCUMENTS

| EP | 0 953 646 A2 | 11/1999 |
| EP | 1 020 525 A1 | 7/2000 |
| EP | 1 457 558 A1 | 9/2004 |
| JP | 9-252778 | 9/1997 |
| WO | WO 99/19493 A2 | 4/1990 |
| WO | WO 97/04089 A2 | 2/1997 |
| WO | 0 770 682 A2 | 5/1997 |
| WO | WO 97/32011 A1 | 9/1997 |
| WO | WO 98/20144 A2 | 5/1998 |
| WO | WO 98/33927 A1 | 8/1998 |
| WO | WO 00/00585 A2 | 1/2000 |
| WO | WO 01/12825 A1 | 2/2001 |
| WO | WO 01/68826 A2 | 9/2001 |
| WO | WO 03/040370 A1 | 5/2003 |

OTHER PUBLICATIONS

S. B. Ha et al., "The plastidic *Arabidopsis* protoporphyrinogen IX oxidase gene, with or without the transit sequence, confers resistance to the diphenyl ether herbicide in rice", Plant, Cell and Environment, vol. 27, No. 1, 2003, pp. 79-88.

A.R.K. Prasad et al., "Generation of Resistance to the Diphenyl Ether Herbicide Acifluorfen by Mel Cells", Biochemical and Biophysical Research Communications, vol. 215, No. 1, Oct. 4, 1995, pp. 186-191.

Daniele Werck-Reichert et al., "Cytochromes P450 for engineering herbicide tolerance", Trends in Plant Science, vol. 5, No. 3, Mar. 2000, pp. 116-123.

Hideo Ohkawa et al., "The use of cytochrome P450 genes to introduce herbicide tolerance in crops: a review"; Pesticide Science, vol. 55, 1999, pp. 867-874.

* cited by examiner

*Primary Examiner*—David H Kruse
(74) *Attorney, Agent, or Firm*—Foley & Lardner LLP

(57) ABSTRACT

The present invention provides a plant on which resistance to at least one of protoporphyrinogen IX oxidize inhibitory-type herbicidal compounds is conferred, wherein to said plant (1) a DNA encoding a protein showing protoporphyrinogen IX oxidize activity and (2) a DNA encoding cytochrome P450 showing activity of metabolizing said herbicidal compound, have been introduced and expressed, and the like.

9 Claims, 5 Drawing Sheets

Fig. 3

```
         EcoRI  SacI                          SalI  HindIII
          ┌─────┬──────────────────────────────┬─────┐
          │     │     DNA(sPPOav)              │     │
          │     └──────────────────────────────┘     │
         ╱                                            ╲
        │              pKFGMP03                       │
         ╲                                            ╱
          ■────────                       ────■
         ColE1                             Km^r
          ori
```

Fig. 4

```
    HindIII NotI    SacI                      SalI  NotI  EcoRI
      ┌─────┬───────┬──────────────────────────┬─────┬─────┐
      │     │CR16G6p│    DNA(sPPOav)           │CR16t│     │
      │     └───────┴──────────────────────────┴─────┘     │
     ╱                                                      ╲
    │            pSUM-NdG6-sPPOav                            │
     ╲                                                      ╱
      ■────────                              ────■
      ColE1                                   Amp^r
       ori
```

US 7,563,950 B2

HERBICIDAL COMPOUND RESISTANT PLANT

BACKGROUND OF THE INVENTION

1. Field of the Invention

The present invention relates to a herbicidal compound resistant plant.

2. Description of the Related Art

Protoporphyrinogen IX oxidize inhibitory-type herbicidal compound is contained as an active ingredient in a weed control agent. As a plant on which resistance to the protoporphyrinogen IX oxidize inhibitory-type herbicidal compound has been conferred, for instance, (1) a plant overexpressing protoporphyrinogen IX oxidize in the plant body, (2) a plant expressing a variant protoporphyrinogen IX oxidize in the plant body, wherein mutation has been introduced to the amino acid sequence of said protoporphyrinogen IX oxidize such that the sensitivity to a protoporphyrinogen IX oxidize inhibitory-type herbicidal compound is reduced (for example, described in International Patent Publication 97/32011 and the like), (3) a plant expressing cytochrome P-450 derived from *actinomyces* such that a protoporphyrinogen IX oxidize inhibitory-type herbicidal compound is metabolized for inactivation in the plant body (for example, described in International Patent Publication 03/40370) and the like are known.

SUMMARY OF THE INVENTION

As to the above herbicidal compound resistant plant, phytotoxicity from the herbicidal compound tends to occur, since herbicidal action of the herbicidal compound is generally immediate. Therefore, it has been desired to develop a plant in which phytotoxicity from the herbicidal compound is further reduced.

The present invention provides a plant on which a synergistic resistance to the herbicidal compound has been conferred by introducing in to the plant combination of two kinds of proteins with different functions. Namely, the present invention provides, 1. a plant on which resistance to at least one of protoporphyrinogen IX oxidize inhibitory-type herbicidal compounds is conferred, wherein to said plant both of the following DNAs have been introduced and expressed (hereinafter, may be referred to as the plant of the present invention):
   (1) a DNA comprising a nucleotide sequence encoding an amino acid sequence of a protein showing protoporphyrinogen IX oxidize activity, and
   (2) a DNA comprising a nucleotide sequence encoding an amino acid sequence of cytochrome P450 showing activity of metabolizing said herbicidal compound;

2. the plant of the above 1, wherein said protein showing protoporphyrinogen IX oxidize activity and said cytochrome P450 showing activity of metabolizing said herbicidal compound in combination in said plant results in synergistic resistance to said herbicidal compound;

3. the plant of the above 1 or 2, wherein said cytochrome P450 is cytochrome P450 derived from *actinomyces:*

4. the plant of the above 1 or 2, wherein said cytochrome P450 is selected from the group consisting of:
   (1) cytochrome P450 derived from *actinomyces* belonging to *Streptomyces,*
   (2) cytochrome P450 comprising an amino acid sequence having 90% or more sequence homology to the amino acid sequence of SEQ ID NO: 1 or 2,
   (3) cytochrom P450 comprising the amino acid sequence of SEQ ID NO: 1, and
   (4) cytochrome P450 comprising the amino acid sequence of SEQ ID NO: 2;

5. the plant of any one of the above 1 to 4, wherein said protein showing protoporphyrinogen IX oxidize activity is a protein derived from a plant and showing protoporphyrinogen IX oxidize activity;

6. the plant of any one of the above 1 to 4, wherein said protein showing protoporphyrinogen IX oxidize activity is
   (1a) a protein derived from a plant and showing protoporphyrinogen IX oxidize activity that is inhibited by said herbicidal compound, or
   (1b) a protein derived from a plant and showing protoporphyrinogen IX oxidize activity that is not inhibited by said herbicidal compound;

7. a method for producing a herbicidal compound resistant plant comprising a step of propagating the plant of any one of the above 1 to 6;

8. a method for controlling weeds comprising a step of applying to a cultivation area of the plant of any one of the above 1 to 6, a compound to which said plant exhibit resistance, (hereinafter, may be referred to as the method for controlling weeds of the present invention);

9. a method for selecting a herbicidal compound resistant plant, said method comprising:
   1) a step of applying or adding to a cultivation area of the plant of any one of the above 1 to 6, a compound to which said plant exhibit resistance, and
   2) a step of selecting a plant which has survived the weed control effect of said applied or added compound; and 10. a method for conferring on a plant, resistance to at least one of protoporphyrinogen IX oxidize inhibitory-type herbicidal compound, said method comprising a step of introducing to and expressing in said plant both of the following DNAs:
    (1) a DNA comprising a nucleotide sequence encoding an amino acid sequence of a protein showing protoporphyrinogen IX oxidize activity, and
    (2) a DNA comprising a nucleotide sequence encoding an amino acid sequence of cytochrome P450 showing activity of metabolizing said herbicidal compound;

and the like.

BRIEF DESCRIPTION OF THE DRAWINGS

FIG. 3 shows the restriction map of the plasmid pKF-GMP03.

FIG. 4 shows the restriction map of the plasmid pSUM-NdG6-sPPOav.

Figure 1:
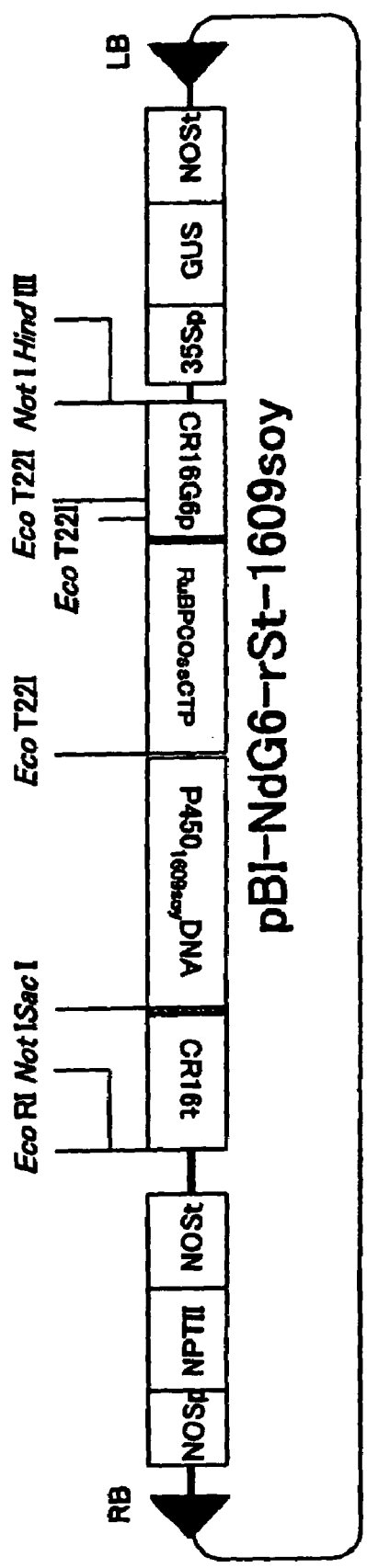
FIG. 1 shows the restriction map of the plasmid pBI-NdG6-rSt-1609soy.

The abbreviations described in the above figures are explained below.

$P450_{1609soy}$DNA: the DNA encoding cytochrom P450 comprising the amino acid sequence of SEQ ID NO: 1.
$P450_{1584soy}$DNA: the DNA encoding cytochrom P450 comprising the amino acid sequence of SEQ ID NO: 2.
RuBPCOssCTP: the nucleotide sequence encoding the chloroplast transit peptide of the small subunit of ribulose-1,5-bisphosphate carboxylase of soybean (cv. Jack).
CR16G6p: DNA in which the nucleotide sequence upstream of restriction site of the restriction enzyme NdeI is removed from the CR16G6 promoter.
CR16t: DNA in which the nucleotide sequence downstream of restriction site of the restriction enzyme ScaI is removed from the CR16 terminator.
NOSp: promoter of the nopaline synthase gene.
NPTII: kanamycin resistance gene.
NOSt: terminator of nopaline synthase gene.
35Sp: 35S promoter of cauliflower mosaic virus.
GUS: β-glucuronidase gene.
RB: the right border sequence of T-DNA.
LB: the left border sequence of T-DNA.
ColE1 ori: the replication origin of plasmid ColE1
$Km^r$: kanamycin resistance gene.
DNA (sPPOav): the DNA having a nucleotide sequence encoding an amino acid sequence of a variant soybean PPO (sPPOav).
HindIII, EcoRI, EcoT221, SacI, NotI, SalI: the cleavage sites of the respective restriction enzyme.

DETAILED DESCRIPTION OF THE PREFERRED EMBODIMENTS

The present invention relates to a plant on which resistance to at least one of protoporphyrinogen IX oxidize inhibitory-type herbicidal compounds is conferred, wherein to said plant both of the following DNAs have been introduced and expressed (hereinafter, may be referred to as the plant of the present invention): (1) a DNA comprising a nucleotide sequence encoding an amino acid sequence of a protein showing protoporphyrinogen LX oxidize activity, and (2) a DNA comprising a nucleotide sequence encoding an amino acid sequence of cytochrome P450 showing activity of metabolizing said herbicidal compound.

The present invention relates to a plant, wherein the protein showing protoporphyrinogen IX oxidize activity and the cytochrome P450 showing activity of metabolizing said herbicidal compound in combination in said plant results in synergistic resistance to said herbicidal compound.

The cytochrome P450 can be cytochrome P450 derived from actinomyces. For example, the cytochrome P450 can be (1) cytochrome P450 derived from actinomyces belonging to Streptomyces, (2) cytochrome P450 comprising an amino acid sequence having 90% or more sequence homology to the amino acid sequence of SEQ ID NO: 1 or 2, (3) cytochrom P450 comprising the amino acid sequence of SEQ ID NO: 1, and (4) cytochrome P450 comprising the amino acid sequence of SEQ ID NO: 2.

The protein showing protoporphyrinogen IX oxidize activity can be a protein derived from a plant and showing protoporphyrinogen LX oxidize activity. For example, the protein showing protoporphyrinogen IX oxidize activity can be (1a) a protein derived from a plant and showing protoporphyrinogen IX oxidize activity that is inhibited by said herbicidal compound, or (1b) a protein derived from a plant and showing protoporphyrinogen IX oxidize activity that is not inhibited by said herbicidal compound.

In another embodiment, the present invention relates to a method for producing a herbicidal compound resistant plant comprising a step of propagating the plant of the present invention.

In another embodiment, the present invention relates to a method for controlling weeds comprising a step of applying to a cultivation area of the plant of the present invention, a compound to which said plant exhibit resistance, (hereinafter, may be referred to as the method for controlling weeds of the present invention).

In another embodiment, the present invention relates to a method for selecting a herbicidal compound resistant plant, by 1) a step of applying or adding to a cultivation area of the plant of the present invention, a compound to which said plant exhibit resistance, and 2) a step of selecting a plant which has survived the weed control effect of said applied or added compound; and In another embodiment, the present invention relates to a method for conferring on a plant, resistance to at least one of protoporphyrinogen IX oxidize inhibitory-type herbicidal compound, the method comprising a step of introducing to and expressing in the plant both of the following DNAs: (1) a DNA comprising a nucleotide sequence encoding an amino acid sequence of a protein showing protoporphyrinogen IX oxidize activity, and (2) a DNA comprising a nucleotide sequence encoding an amino acid sequence of cytochrome P450 showing activity of metabolizing said herbicidal compound.

Hereinafter, the present invention will be described in detail.

The weed control agent in the present invention is a composition for weed control containing a herbicidal compound as an active ingredient. The composition may contain as needed insecticidal compounds, fungicidal compounds, plant growth regulatory compounds, fertilizer ingredients and the like along with the herbicidal compound. As such weed control agents, for example, there are compositions containing as an active ingredient a compound inhibiting porphyrin biosynthesis and the like. As the compounds inhibiting porphyrin biosynthesis, for example, there are compounds inhibiting activity of protoporphyrinogen IX oxidize (EC 1.13.11.27, hereinafter may be referred to as PPO) and the like. Specifically for example, as the compounds inhibiting activity of PPO (hereinafter, may be referred to as the present herbicidal compounds), there are the compounds disclosed in Duke, S. O., Rebeiz, C. A. ACS Symposium Series 559, Porphyric Pesticides, Chemistry, Toxicology, and Pharmaceutical Applications. American Chemical Society, Washington D.C. (1994) and the like. In the present herbicidal compounds, various molecular species having different structures are contained (Duke et al., Weed Sci. 39: p 465 (1991); Nandihalli et al., Pesticide Biochem. Physiol. 43: p 193 (1992); Matringe et al., FEBS Lett. 245: p 35 (1989); Yanase, Andoh, Pesticide Biochem. Physiol. 35: p 70 (1989)), there may be, for example, diphenylether:

for instance, chloromethoxynil, biphenox, chloronitrophene (CNP), acifluorfen (i.e. 5-[2-chloro-4-(trifluoromethyl)phenoxy]-2-nitrobenzoic acid and the like) and it's ethyl ester, acifluorfen-sodium, oxyfluorfen (i.e. 2-chloro-1-(3-ethoxy-4-nitrophenoxy)-4-trifluoromethylbenzene), or oxadiazol (for instance, oxadiazon (i.e. 3-[2,4-dichloro-5-(1-methylethoxy)phenyl]-5-(1,1-dimethylethyl)-1,3,4-oxadiazol-2(3H)-one) and the like);

cyclic imide:

for instance, S-23142 (i.e. N-(4-chloro-2-fluoro-5-propargyloxyphenyl)-3,4,5,6-tetrahydrophtalimide and the like), or chlorphthalim (i.e. N-(4-chlorophenyl)-3,4,5,6-tetrahydrophtalimide); phenylpyrazole:

for instance, TNPP-ethyl (i.e. ethyl 2-[1-(2,3,4-trichlorophenyl)-4-nitropyrazolyl-5-oxy]propionate) and the like;

pyridine derivatives for instance, LS82-556 (i.e. N3-(1-phenylethyl)-2,6-dimethyl-5-propyonylnicotinamide) and the like;

phenopylate, o-phenylpyrrolidinocarbamate analog of phenopylate, or piperidinocarbamate analog of phenopylate and the like.

As the present herbicidal compounds, there may be, specifically for example, a compound of the following formula (I):

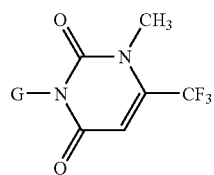
(I)

wherein in formula (I) G represents a group shown in any one of the following G-1 to G-9;

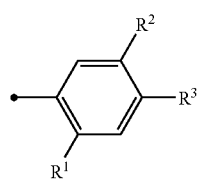
G-1

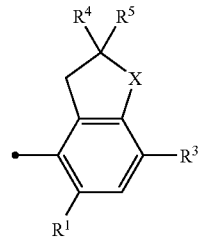
G-2

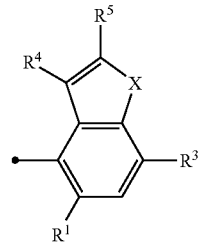
G-3

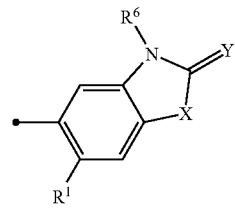
G-4

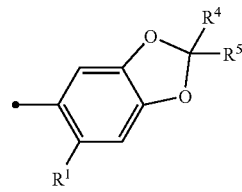
G-5

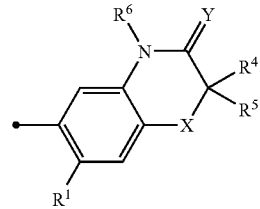
G-6

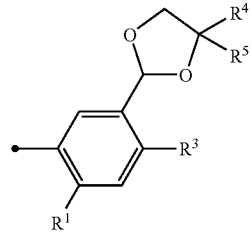
G-7

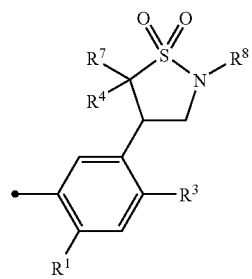
G-8

-continued

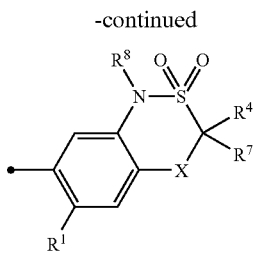
G-9 wherein in G-1 to G-9,
X represents an oxygen atom or sulfur atom;
Y represents an oxygen atom or sulfur atom;
$R^1$ represents a hydrogen atom or halogen atom;
$R^2$ represents a hydrogen atom, $C_1$-$C_8$ alkyl group, $C_1$-$C_8$ haloalkyl group, halogen atom, hydroxyl group, —$OR^9$ group, —SH group, —$S(O)pR^9$ group, —$COR^9$ group, —$CO_2R^9$ group, —$C(O)SR^9$ group, —$C(O)NR^{11}R^{12}$ group, —$CONH_2$ group, —CHO group, —$CR^9$=$NOR^{18}$ group, —CH=$CR^{19}CO_2R^9$ group, —$CH_2CHR^{19}CO_2R^9$ group, —$CO_2N$=$CR^{13}R^{14}$ group, nitro group, cyano group, —$NHSO_2R^{15}$ group, —$NHSO_2NHR^{15}$ group, —$NR^9R^{20}$ group, —$NH_2$ group or phenyl group that may be substituted with one or more $C_1$-$C_4$ alkyl groups which may be the same or different;
p represents 0, 1 or 2;
$R^3$ represents $C_1$-$C_2$ alkyl group, $C_1$-$C_2$ haloalkyl group, —$OCH_3$ group, —$SCH_3$ group, —$OCHF_2$ group, halogen atom, cyano group, nitro group or $C_1$-$C_3$ alkoxy group substituted with a phenyl group which may be substituted on the ring with at least one substituent selected from a halogen atom, $C_1$-$C_3$ alkyl group, $C_1$-$C_3$ haloalkyl group, $OR^{28}$ group, $NR^{11}R^{28}$ group, $SR^{28}$ group, cyano group, $CO_2R^{28}$ group and nitro group;
$R^4$ represents a hydrogen atom, $C_1$-$C_3$ alkyl group or $C_1$-$C_3$ haloalkyl group;
$R^5$ represents a hydrogen atom, $C_1$-$C_3$ alkyl group, $C_1$-$C_3$ haloalkyl group, cyclopropyl group, vinyl group, $C_2$ alkynyl group, cyano group, —$C(O)R^{20}$ group, —$CO_2R^{20}$ group, —$C(O)NR^{20}R^{21}$ group, —$CHR^{16}R^{17}CN$ group, —$CR^{16}R^{17}C(O)R^{20}$ group, —$C^{16}R^{17}CO_2R^{20}$ group, —$CR^{16}R^{17}C(O)NR^2OR^{21}$ group, —$CHR^{16}OH$ group, —$CHR^{16}OC(O)R^{20}$ group or —$OCHR^{16}OC(O)NR^{20}R^{21}$ group, or, when G represents G-2 or G-6, $R^4$ and $R^5$ may represent C=O group together with the carbon atom to which they are attached;
$R^6$ represents $C_1$-$C_6$ alkyl group, $C_1$-$C_6$ haloalkyl group, $C_2$-$C_6$ alkoxyalkyl group, $C_3$-$C_6$ alkenyl group or $C_3$-$C_6$ alkynyl group;
$R^7$ represents a hydrogen atom, $C_1$-$C_6$ alkyl group, $C_1$-$C_6$ haloalkyl group, halogen atom, —$S(O)_2(C_1$-$C_6$ alkyl) group or —$C(=O)R^{22}$ group;
$R^8$ represents a hydrogen atom, $C_1$-$C_8$ alkyl group, $C_3$-$C_8$ cycloalkyl group, $C_3$-$C_8$ alkenyl group, $C_3$-$C_8$ alkynyl group, $C_1$-$C_8$ haloalkyl group, $C_2$-$C_8$ alkoxyalkyl group, $C_3$-$C_8$ alkoxyalkoxyalkyl group, $C_3$-$C_8$ haloalkynyl group, $C_3$-$C_8$ haloalkenyl group, $C_1$-$C_8$ alkylsulfonyl group, $C_1$-$C_8$ haloalkylsulfonyl group, $C_3$-$C_8$ alkoxycarbonylalkyl group, —$S(O)_2NH(C_1$-$C_8$ alkyl) group, —$C(O)R^{23}$ group or benzyl group which may be substituted with $R^{24}$ on the phenyl ring;
$R^9$ represents $C_1$-$C_8$ alkyl group, $C_3$-$C_8$ cycloalkyl group, $C_3$-$C_8$ alkenyl group, $C_3$-$C_8$ alkynyl group, $C_1$-$C_8$ haloalkyl group, $C_2$-$C_8$ alkoxyalkyl group, $C_2$-$C_8$ alkylthioalkyl group, $C_2$-$C_8$ alkylsulfinylalkyl group, $C_2$-$C_8$ alkylsulfonylalkyl group, $C_4$-$C_8$ alkoxyalkoxyalkyl group, $C_4$-$C_8$ cycloalkylalkyl group, $C_4$-$C_8$ cycloalkoxyalkyl group, $C_4$-$C_8$ alkenyloxyalkyl group, $C_4$-$C_8$ alkynyloxyalkyl group, $C_3$-$C_8$ haloalkoxyalkyl group, $C_4$-$C_8$ haloalkenyloxyalkyl group, $C_4$-$C_8$ haloalkynyloxyalkyl group, $C_4$-$C_8$ cycloalkylthioalkyl group, $C_4$-$C_8$ alkenylthioalkyl group, $C_4$-$C_8$ alkynylthioalkyl group, $C_1$-$C_4$ alkyl group substituted with a phenoxy group which may be substituted on the ring with at least one substituent selected from a halogen atom, $C_1$-$C_3$ alkyl group and $C_1$-$C_3$ haloalkyl group, $C_1$-$C_4$ alkyl group substituted with a benzyloxy group which may be substituted on the ring with at least one substituent selected from a halogen atom, $C_1$-$C_3$ alkyl group and $C_1$-$C_3$ haloalkyl group, $C_4$-$C_8$ trialkylsilylalkyl group, $C_2$-$C_8$ cyanoalkyl group, $C_3$-$C_8$ halocycloalkyl group, $C_3$-$C_8$ haloalkenyl group, $C_5$-$C_8$ alkoxyalkenyl group, $C_3$-$C_8$ haloalkoxyalkenyl group, $C_5$-$C_8$ alkylthioalkenyl group, $C_3$-$C_8$ haloalkynyl group, $C_5$-$C_8$ alkoxyalkynyl group, $C_5$-$C_8$ haloalkoxyalkynyl group, $C_5$-$C_8$ alkylthioalkynyl group, $C_2$-$C_8$ alkylcarbonyl group, benzyl group which may be substituted on the ring with at least one substituent selected from a halogen atom, $C_1$-$C_3$ alkyl group, $C_1$-$C_3$ haloalkyl group, —$OR^{28}$ group, —$NR^{11}R^{28}$ group, —$SR^{26}$ group, cyano group, —$CO_2R^{28}$ group and nitro group, —$CR^{16}R^{17}COR^{10}$ group, —$CR^{16}R^{17}CO_2R^{20}$ group, —$CR^{16}R^{17}P(O)(OR^{10})_2$ group, —$CR^{16}R^{17}P(S)(OR^{10})_2$ group, —$CR^{16}R^{17}C(O)NR^{11}R^{12}$ group, —$CR^{16}R^{17}C(O)NH_2$ group, —$C(=CR^{26}R^{27})COR^{10}$ group, —$C(=CR^{26}R^{27})CO_2R^{20}$ group, $C(=CR^{26}R^{27})P(O)(OR^{10})_2$ group, —$C(=CR^{26}R^{27})P(S)(OR^{10})_2$ group, —$C(=CR^{26}R^{27})C(O)NR^{11}R^{12}$ group, —$C(=CR^{26}R^{27})C(O)NH_2$ group, or any one of rings shown in Q-1 to Q-7:

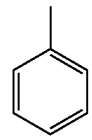
Q-1

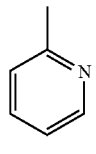
Q-2

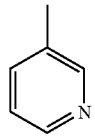
Q-3

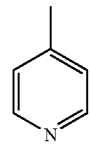
Q-4

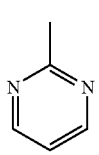
Q-5

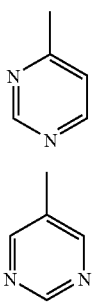

Q-6

Q-7

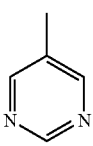

which may be substituted on the ring with at least one substituent selected from a halogen atom, $C_1$-$C_6$ alkyl group, $C_1$-$C_6$ haloalkyl group, $C_2$-$C_6$ alkenyl group, $C_2$-$C_6$ haloalkenyl group, $C_2$-$C_6$ alkynyl group, $C_3$-$C_6$ haloalkynyl group, $C_2$-$C_8$ alkoxyalkyl group, —$OR^{28}$ group, —$SR^{28}$ group, —$NR^{11}R^{28}$ group, $C_3$-$C_8$ alkoxycarbonylalkyl group, $C_2$-$C_4$ carboxyalkyl group, —$CO_2R^{28}$ group and cyano group;

$R^{10}$ represents a $C_1$-$C_6$ alkyl group, $C_2$-$C_6$ alkenyl group, $C_3$-$C_6$ alkynyl group or tetrahydrofuranyl group;

$R^{11}$ and $R^{13}$ independently represent a hydrogen atom or $C_1$-$C_4$ alkyl group:

$R^{12}$ represents $C_1$-$C_6$ alkyl group, $C_3$-$C_6$ cycloalkyl group, $C_3$-$C_6$ alkenyl group, $C_3$-$C_6$ alkynyl group, $C_2$-$C_6$ alkoxyalkyl group, $C_1$-$C_6$ haloalkyl group, $C_3$-$C_6$ haloalkenyl group, $C_3$-$C_6$ haloalkynyl group, phenyl group which may be substituted on the ring with at least one substituent selected from a halogen atom, $C_1$-$C_4$ alkyl group and $C_1$-$C_4$ alkoxy group or —$CR^{16}R^{17}CO_2R^{25}$ group; or, $R^{11}$ and $R^{12}$ together may represent —$(CH_2)_5$—, —$(CH_2)_4$— or —$CH_2CH_2OCH_2CH_2$—, or in that case the resulting ring may be substituted with a substituent selected from a $C_1$-$C_3$ alkyl group, a phenyl group and benzyl group;

$R^{14}$ represents a $C_1$-$C_4$ alkyl group or phenyl group which may be substituted on the ring with a substituent selected from a halogen atom, $C_1$-$C_3$ alkyl group and $C_1$-$C_3$ haloalkyl group; or, $R^{13}$ and $R^{14}$ may represent $C_3$-$C_8$ cycloalkyl group together with the carbon atom to which they are attached;

$R^{15}$ represents $C_1$-$C_4$ alkyl group, $C_1$-$C_4$ haloalkyl group or $C_3$-$C_6$ alkenyl group;

$R^{16}$ and $R^{17}$ independently represent a hydrogen atom or $C_1$-$C_4$ alkyl group, $C_1$-$C_4$ haloalkyl group, $C_2$-$C_4$ alkenyl group, $C_2$-$C_4$ haloalkenyl group, $C_2$-$C_4$ alkynyl group, $C_3$-$C_4$ haloalkynyl group; or, $R^{16}$ and $R^{17}$ may represent $C_3$-$C_6$ cycloalkyl group with the carbon atom to which they are attached, or the ring thus formed may be substituted with at least one substituent selected from a halogen atom, a $C_1$-$C_3$ alkyl group and $C_1$-$C_3$ haloalkyl group;

$R^{18}$ represents a hydrogen atom, $C_1$-$C_6$ alkyl group, $C_3$-$C_6$ alkenyl group or $C_3$-$C_6$ alkynyl group;

$R^{19}$ represents a hydrogen atom, $C_1$-$C_4$ alkyl group or halogen atom, $R^{20}$ represents a hydrogen atom, $C_1$-$C_6$ alkyl group, $C_3$-$C_6$ cycloalkyl group, $C_3$-$C_6$ alkenyl group, $C_3$-$C_6$ alkynyl group, $C_2$-$C_6$ alkoxyalkyl group, $C_1$-$C_6$ haloalkyl group, $C_3$-$C_6$ haloalkenyl group, $C_3$-$C_6$ haloalkynyl group, phenyl group which may be substituted on the ring with at least one substituent selected from a halogen atom, $C_1$-$C_4$ alkyl group and —$OR^{28}$ group, or —$CR^{16}R^{17}CO_2R^{25}$ group;

$R^{21}$ represents a hydrogen atom, $C_1$-$C_2$ alkyl group or —$CO_2(C_1$-$C_4$ alkyl) group;

$R^{22}$ represents a hydrogen atom, $C_1$-$C_6$ alkyl group, $C_1$-$C_6$ alkoxy group or NH($C_1$-$C_6$ alkyl) group;

$R^{23}$ represents $C_1$-$C_6$ alkyl group, $C_1$-$C_6$ haloalkyl group, $C_1$-$C_6$ alkoxy group, NH($C_1$-$C_6$ alkyl) group, benzyl group, $C_2$-$C_8$ dialkylamino group or phenyl group which may be substituted with $R^{24}$;

$R^{24}$ represents $C_1$-$C_6$ alkyl group, 1 to 2 halogen atoms, $C_1$-$C_6$ alkoxy group or $CF_3$ group;

$R^{25}$ represents $C_1$-$C_6$ alkyl group, $C_1$-$C_6$ haloalkyl group, $C_3$-$C_6$ alkenyl group, $C_3$-$C_6$ haloalkenyl group, $C_3$-$C_6$ alkynyl group or $C_3$-$C_6$ haloalkynyl group;

$R^{26}$ and $R^{27}$ each represent independently a hydrogen atom, $C_1$-$C_4$ alkyl group, $C_1$-$C_4$ haloalkyl group, $C_2$-$C_4$ alkenyl group, $C_2$-$C_4$ haloalkenyl group, $C_2$-$C_4$ alkynyl group, $C_3$-$C_4$ haloalkynyl group, —$OR^{28}$ group, —$NHR^{28}$ group, or —$SR^{28}$ group; or, $R^{26}$ and $R^{27}$ may represent $C_3$-$C_8$ cycloalkyl group with the carbon atom to which they are attached, or each of the ring thus formed may be substituted with at least one substituent selected from a halogen atom, $C_1$-$C_3$ alkyl group and $C_1$-$C_3$ haloalkyl group; and, $R^{28}$ represents a hydrogen atom, $C_1$-$C_6$ alkyl group, $C_1$-$C_6$ haloalkyl group, $C_3$-$C_6$ alkenyl group, $C_3$-$C_6$ haloalkenyl group, $C_3$-$C_6$ alkynyl group, $C_3$-$C_6$ haloalkynyl group, $C_2$-$C_4$ carboxyalkyl group, $C_3$-$C_8$ alkoxycarbonylalkyl group, $C_3$-$C_8$ haloalkoxycarbonylalkyl group, $C_5$-$C_9$ alkenyloxycabonylalkyl group, $C_5$-$C_9$ haloalkenyloxycabonylalkyl group, $C_5$-$C_9$ alkynyloxycabonylalkyl group, $C_5$-$C_9$ haloalkynyloxycabonylalkyl group, $C_5$-$C_9$ cycloalkoxycabonylalkyl group or $C_5$-$C_9$ halocycloalkoxycabonylalkyl group.

And further, there may be, specifically for example, a compound having the following formula (hereinafter, may be referred to as the compound (II)):

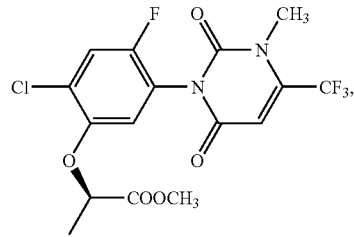

butafenacil, flufenpyr-ethyl, methyl 2-[2-chloro-5-[3,6-dihydro-3-methyl-2,6-dioxo-4-(trifluoromethyl)-1(2H)-pyrimidinyl]-4-fluorophenoxy]phenoxyacetate, ethyl [3-[2-chloro-5-[3,6-dihydro-3-methyl-2,6-dioxo-4-(trifluoromethyl)-1(2H)-2-pyrimizinyl]-4-fluorophenoxy]-2-pyridazinyl] oxyacetate, carfentrazone-ethyl, sulfentrazone and the like.

Here, "butafenacil" is the compound of CAS registry no. 134605-64-4, "flufenpyr-ethyl" is the compound of CAS registry no. 188489-07-8, "carfentrazone-ethyl" is the compound of CAS registry no. 128639-02-1, "sulfentrazone" is the compound of CAS registry no. 122836-35-5. Hereinafter, methyl 2-[2-chloro-5-[3,6-dihydro-3-methyl-2,6-dioxo-4-(trifluorom ethyl)-1(2H)-pyrimidinyl]-4-fluorophenoxy] phenoxyacetate (CAS registry no. 344419-98-3) may be referred to as the compound (III), and ethyl [3-[2-chloro-5-[3,6-dihydro-3-methyl-2,6-dioxo-4-(trifluoro methyl)-1 (2H)-2-pyrimizinyl]-4-fluorophenoxy]-2-pyridazinyl]oxyacetate (CAS registry no. 353292-31-6) may be referred to as the compound (IV).

In the present invention, "sequence homology" refers to the homology between two nucleotide sequences or two amino acid sequences. Such "sequence homology" may be determined by comparing the two sequences, each aligned in an optimal state, over the whole region of the test sequences. As such, additions or deletions (for example, gaps) can be utilized in the optimal alignment of the test nucleic acid sequences or amino acid sequences. Such sequence homology can be calculated through the step of producing the alignment conducted by a homology analysis using a program such as FASTA (Pearson & Lipman, Proc. Natl. Acad. Sci. USA, 4, 2444-2448 (1988)), BLAST (Altschul et al., Journal of Molecular Biology, 215, 403-410 (1990)), CLUSTAL W (Thompson, Higgins & Gibson, Nucleic Acid Research, 22, 4673-4680 (1994a)) and the like. Such programs, for example, can be typically utilized on the webpage of the DNA Data Bank of Japan (the international databank operated within the Center for Information Biology and DNA Data Bank of Japan). Further, the sequence homology may be determined by utilizing a commercially available sequence analysis software. Specifically for example, it can be calculated by producing an alignment conducted by a homology analysis by the Lipman-Pearson method (Lipman, D. J. and Pearson, W. R., Science, 227, 1435-1441, (1985)) utilizing GENETYX-WIN Ver. 6 (manufactured by GENETYX Corporation). For example, as the results of alignment at homology analysis of the amino acid sequence of SEQ ID NO: 1 and the amino acid sequence of SEQ ID NO: 2 by using the method, it is calculated 90% of sequence homology.

As the gene (DNA) having a nucleotide sequence encoding an amino acid sequence of "the protein showing protoporphyrinogen IX oxidize activity" used in the present invention, for example, there are a gene having a nucleotide sequence encoding an amino acid sequence of a wild-type PPO (for instance, refer to U.S. Pat. No. 5,767,373 and the like), a gene having a nucleotide sequence encoding an amino acid sequence of a variant PPO having PPO activity that is not inhibited by the present herbicidal compound (for instance, refer to U.S. Pat. No. 5,939,602, WO 9704089 and the like), a gene having a nucleotide sequence encoding an amino acid sequence of PPO derived from bacterium having PPO activity that is not inhibited by the present herbicidal compound (for instance, refer to EPO 0770682, WO 9833927 and the like) and the like. These genes may be a gene having a nucleotide sequence encoding an amino acid sequence of naturally-occurring PPO, a gene having a nucleotide sequence encoding an amino acid sequence of a protein having PPO activity wherein substitution, addition or deletion and the like of 1 or more amino acids has been introduced to the amino acid sequence of naturally-occurring PPO, or a gene having a nucleotide sequence encoding an amino acid sequence of a protein selected based on PPO activity. Also, these genes may be a gene having a nucleotide sequence encoding an amino acid sequence of a protein having PPO activity that is inhibited by the present herbicidal compound in an amount to inhibit natural PPO activity of plant or a gene having a nucleotide sequence encoding an amino acid sequence of a protein having PPO activity that is not inhibited by the present herbicidal compound. Concretely, as the gene having a nucleotide sequence encoding an amino acid sequence of naturally-occurring PPO, there are, for example, genes derived from *Esherichia coli* (Genbank accession X68660), *Bacillus subtilis* (Genbank accession X97208), *Haemophilus influnzae* (Genbank accession L42023), mouse (Genbank accession D45185), human (Genbank accession D38537), *Arabidopsis* (Genbank accession D83139) or tobacco (Genbank accession Y13465, Y13466) and the like. Such gene used in the present invention has a nucleotide sequence encoding an amino acid sequence of a protein which shows PPO activity and can confer on a plant resistance to the present herbicidal compound when said gene and a cytochrome P450 gene (DNA) showing herbicidal compound metabolizing activity described hereinafter were introduced to and expressed in the plant to utilize said gene in combination with the cytochrome P450 gene.

Cytochrome P450 used in the present invention is a family of proteins containing protoheme and named for its spectroscopic property indicating Soret near 450 nm when it binds with carbon monoxide at a reduction state. The cytochrome P450 exists in various animal tissues, plant tissues, fungi, yeast and bacteria. The cytochrome p450 has abilities to catalyze, with free oxygen and 2 electrons generally derived from NADPH, or rarely derived from NADH, monooxygenation of the present herbicidal compounds and the like and subsequent elimination of functional groups. The cytochrome p450 may be (1) a type to be provided electron from the electron transfer system with both of ferredoxin and NADPH-ferredoxin reductase, or (2) a type to be provided electron directly from NADPH-cytochrome P450 reductase. Preferably, it may be the former. The cytochrome P450 in the former may be located in any one of subcellular organelles of a host cell or in the cytoplasm. The ferredoxin may be an endogenous ferredoxin in the host cell or a foreign ferredoxin produced in the host cell wherein a foreign ferredoxin gene has been introduced into the host cell.

Preferable cytochrome P450 used in the present invention may be cytochrome P450 derived from *actinomyces*. Here, "*actinomyces*" is a family of prokaryote belonging to the Actinomycetales, which are a family of Gram-positive bacteria to be grouped 8 genera of *Streptomyces*. Actinomyces, *Mycobacterium, Frankia, Nocardia* and the like. More preferable cytochrome P450 may be cytochrome P450 derived from *actinomyces* belonging to *Streptomyces*, concretely, for example, cytochrome P450 derived from *Streptomyces phaeochromogenes, Streptomyces testaceus, Streptomyces achromogenes, Streptomyces griseofuscus, Streptomyces thermocoerulescens, Streptomyces nogalater, Streptomyces tsusimaensis, Streptomyces glomerochromogenes, Streptomyces olivochromogenes, Streptomyces ornatus, Streptomyces griseus, Streptomyces lanatus, Streptomyces misawanensis, Streptomyces pallidus, Streptomyces roseorubens, Streptomyces rutgersensis, Streptomyces steffisburgensis, Saccharopolyspora taberi* and the like. Concrete examples of cytochrome P450 derived from *actinomyces* belonging to *Streptomyces* may be cytochrome P450 having the amino acid sequence of SEQ ID NO: 1, cytochrome P450 having the amino acid sequence of SEQ ID NO: 2, cytochrome P450 having an amino acid sequence having 90% or more sequence homology with the amino acid sequence of SEQ ID NO: 1 or 2, and the like.

The gene (DNA) having a nucleotide sequence encoding an amino acid sequence of cytochrome P450 may be a cytochrome P450 gene having naturally-occurring nucleotide sequence, and a gene having a nucleotide sequence encoding cytochrome P450 in which the codon usage has been optimized for its expression in the host cell. Also, it may be a gene encoding a protein having cytochrome P450 activity wherein substitution, addition, deletion or the like of amino acid has been introduced to an amino acid sequence of a naturally-occurring cytochrome P450, and, a gene encoding a protein selected based on the cytochrome P450 activity. Concretely, the gene encoding cytochrome P450 may be a gene encoding cytochrome P450 described in International Patent Publication WO 03040370.

The gene having a nucleotide sequence encoding an amino acid sequence of the cytochrome P450 introduced to the host cell may be located in any one of subcellular organelles in the cell or in chromosome in nuclear. Also, the cytochrome P450 may be located in any one of subcellular organelles, cytoplasm or extracellular space, preferably subcellular organelles, more preferably plastid.

For the transition of cytochrome P450 to subcellular organelles in the cell, it may be introduced to the host cell a chimeric DNA in which a DNA having a nucleotide sequence encoding organelles transit peptide sequence is linked in frame upstream of a DNA having a nucleotide sequence encoding an amino acid sequence of cytochrome P450. Here, "linked in frame" means that the reading frame of the nucleotide sequence encoding the organelles transit peptide sequence and the reading frame of the nucleotide sequence encoding the amino acid sequence of the cytochrome P450 are linked to form one continuous reading frame. The transit peptide sequence to transit and localize the protein to subcellular organelles in the host cell is, for example, a transit peptide sequence of a cytoplasmic precursor of a chloroplast protein of a plant described in U.S. Pat. No. 5,717,084, and a chimeric sequence comprising plural kinds of transit peptide sequences described in U.S. RE36449 etc. Concretely, it is, for example, chloroplast transit peptide sequence derived from ribulose-1,5-bisphosphate carboxylase (hereinafter, may be referred to as RuBPCO) small subunit of soybean which is obtainable by a method described in International Patent Publication WO03040370.

As the method of artificially causing deletions, additions or substitutions of amino acid residues in an amino acid sequence of the protein showing PPO activity or an amino acid sequence of the cytochrome P450 described above, for example, there is a method comprising a steps of carrying out site-directed mutagenesis on a DNA having a nucleotide sequence encoding the amino acid sequence, and then allowing the expression of such DNA by a conventional method. Concretely, for example, it may be a method utilizes amber mutations (gapped duplex method, Nucleic Acids Res., 12, 9441-9456 (1984)), a method by PCR utilizing primers for introducing a mutation and the like. Also, for example, it may be a method comprising the steps of carrying out random mutagenesis on a DNA having a nucleotide sequence encoding the amino acid sequence and the like. Concretely, for example, it may be a method of conducting PCR by utilizing the DNA having a nucleotide sequence encoding the amino acid sequence as a template and a primer pair which can amplify the full length of the DNA under the conditions in which concentration of each of dATP, dTTP, dGTP and dCTP utilized as a substrate are changed, or, under the conditions in which the concentration of $Mg^{2+}$ is made increase more to promote the polymerase reaction, and the like. Such methods of PCR may be, for example, the conventional methods described in Method in Molecular Biology, (31), 1994, 97-112 and the like.

In the method for confirming PPO activity of the protein to which mutation has been artificially introduced as described above, for example, the DNA having a nucleotide sequence encoding the amino acid sequence of the protein to which the mutation has been artificially introduced is inserted to a vector plasmid firstly, as described in WO9732011 and the like. Next, by introducing the vector plasmid and expressing the DNA in a PPO-deficient host cell, it may be confirmed that the introduced DNA compensates PPO deficiency and the PPO-deficient host cell can be grown heme-independently. Also, in the method for confirming cytochrome P450 activity of the protein to which mutation has been introduced as described above, for example, the DNA having a nucleotide sequence encoding the amino acid sequence of the protein to which the mutation has been introduced is inserted to a vector plasmid firstly. The vector plasmid is introduced in a host cell to express the DNA, as described in WO03040370 and the like. Thus, such activity may be confirmed by adding and reacting the present herbicidal compound as a substrate, ferredoxin and NADPH-ferredoxin reductase to an extract of the host cell in which mutated cytochrome P450 was produced, and measuring the decreased substrate in the reaction mixture after the reaction.

The DNA having a nucleotide sequence encoding an amino acid sequence wherein substitution, addition, deletion or the like of amino acid has been introduced to the particular amino acid sequence of the protein showing PPO activity or the particular amino acid sequence of cytochrome P450 can be obtained from various DNA libraries, by utilizing a polynucleotide having a nucleotide sequence complementary to the nucleotide sequence encoding the particular amino acid sequences described above as a probe and carrying out hybridization under stringent conditions according to the conventional genetic engineering methods. Also, the DNA having a nucleotide sequence encoding an amino acid sequence having 90% or more sequence homology to the particular amino acid sequences, concretely, for example, a DNA having a nucleotide sequence encoding cytochrome P450 having an amino acid sequence having 90% or more sequence homology to the amino acid sequence of SEQ ID NO: 1 or 2 can be obtained from various DNA libraries, by utilizing a polynucleotide having a nucleotide sequence complementary to the nucleotide sequence encoding the particular amino acid sequence as a probe and carrying out hybridization under a stringent condition according to the conventional genetic engineering methods. As the "stringent conditions", there can be mentioned, for example, the conditions under which hybridization is performed at 68° C. in a solution containing 6×SSC (let the solution containing 3 N NaCl and 0.3 M trisodium citrate be 20×SSC) and then the hybridized membrane is washed at 68° C. with 0.1×SSC and 0.5% SDS in a hybridization conducted according to the conventional method described in such as Sambrook, J., Frisch, E. F., and Maniatis, T.; chapter 9.53, Molecular Cloning $2^{nd}$ edition, Cold Spring Harbor Press (1989). The salt concentration in the washing step can be selected, for example, from the conditions of 2×SSC (low stringency condition) to the conditions of 0.1×SSC (high stringency conditions). A temperature in the washing step can be selected, for example, from room temperature (low stringency condition) to 68° C. (high stringency condition). Alternatively, both of the salt concentration and temperature may be changed.

To introduce to plant and express the gene to be introduced in the present invention, generally, a DNA having a nucleotide sequence encoding the amino acid sequence of the protein to be expressed, a DNA in which aforementioned DNA and a promoter functional in the plant cell is operably linked or the like, may be inserted to a vector plasmid functional in the plant cell, and introduced to the plant cell. When the vector plasmid already possessing the promoter functional in the plant cell is utilized, aforementioned DNA may be inserted downstream of the promoter present in the vector plasmid so that the promoter and the DNA having a nucleotide sequence encoding the amino acid sequence of the protein to be expressed are operably linked.

Here, the promoter functional in the host cell such as plant cell is a nucleotide sequence which is connected 5' upstream of a nucleotide sequence of a gene having a nucleotide sequence encoding an amino acid sequence of a protein (the structural gene) and has a function to control initiation of the transcription of the gene in the host cell such as plant cell. As the functional promoter in the plant cell, for example, there is mentioned T-DNA derived constitutive promoters such as nopaline synthase gene promoter and octopine synthase gene promoter; plant virus-derived promoters such as cauliflower mosaic virus derived 19S and 35S promoters; inducible promoters such as phenylalanine ammonia-lyase gene promoter, chalcone synthase gene promoter and pathogenesis-related protein gene promoter; the plant promoter described in International Patent Publication WO2000020613, and the like. Also, a terminator functional in the host cell such as plant cell may be linked downstream of a DNA in which the promoter functional in the host cell such as plant cell described above and a DNA having a nucleotide sequence encoding an amino acid sequence of the protein showing PPO activity or the cytochrome P450 are operably linked.

The terminator functional in the host cell such as plant cell is a nucleotide sequence which is connected 3' downstream of a nucleotide sequence of a gene having a nucleotide sequence encoding an amino acid sequence of a protein (the structural gene) and has a function to add polyadenine sequence for stabilization of the transcription of the gene. As the functional terminator in the plant cell, for example, there is mentioned T-DNA derived constitutive terminators such as nopaline synthase gene (NOS) terminator; plant virus derived terminators such as terminators of garlic virus GV1 or GV2; the plant terminator described in International Patent Publication WO2000020613; and the like.

As the plant cell to be utilized as the host cell, there are, for example, plant cells derived from dicotyledonous plant, including solanaceous plant such as eggplant, potato and tomato; cruciferous plant such as rape, canola, lettuce, sugar beet and *arabidopsis*; leguminous plant such as soybean, pea and alfalfa; rosaceous plant such as apple, pear and almond; citrus such as orange and lemon; cotton, *linum*, sunflower, grape, almond, poplar, and plant cells derived from monocotyledonous plant including poaceous plant such as corn, rice, wheat, barley, rye, oat and sorghum and the like.

As the plant cell to be utilized as the host cell, there are various plant cells such as plant tissues, plant bodies, cultured cells, seeds and the like.

As the method for introducing into a host cell such as a plant cell DNA having the structural gene to which a promoter and a terminator functional in the host cell such as the plant cell are linked, there are, for example, a method by infection with *agrobacterium* (Japanese examined patent publication No. Hei2-58917 and Japanese unexamined patent publication No. Syo-60-70080), electroporation into protoplast (Japanese unexamined patent publication No. Syo-60-251887 and Japanese unexamined patent publication No. Hei5-68575), particle gun methods (Japanese unexamined patent publication No. Hei5-508316 and Japanese unexamined patent publication No. Syo-63-258525) or the like.

In such case, the transformant to which the DNA has been introduced can be selected based on phenotype of a selective marker gene, by simultaneously introducing a selective marker gene selected from hygromycin phosphotransferase gene, neomycin phosphotransferase gene, chloramphenicol acetyltransferase gene and the like, and a DNA having a nucleotide sequence encoding an amino acid sequence of the protein showing PPO activity or a DNA having a nucleotide sequence encoding an amino acid sequence of the cytochrome P450 showing the present herbicidal compound metabolizing activity. The selective marker gene, and the DNA having a nucleotide sequence encoding an amino acid sequence of the protein showing PPO activity or the DNA having a nucleotide sequence encoding an amino acid sequence of the cytochrome P450 showing the present herbicidal compound metabolizing activity may be tandemly inserted into the same vector and introduced. A vector plasmid comprising the selective marker gene, and the DNA having a nucleotide sequence encoding an amino acid sequence of the protein showing PPO activity or the DNA having a nucleotide sequence encoding an amino acid sequence of the cytochrome P450 showing the present herbicidal compound metabolizing activity may be introduced simultaneously. A transformant to which the objective gene has been introduced may also be selected by culturing with a medium containing the present herbicidal compound, plant cells to which a vector comprising the objective gene has been introduced and isolating grown clones.

As a method for introducing into a plant a DNA having a nucleotide sequence encoding an amino acid sequence of the protein showing PPO activity and a DNA having a nucleotide sequence encoding an amino acid sequence of the cytochrome P450 showing the present herbicidal compound metabolizing activity, there may be (1) a method of introducing both of the DNAs simultaneously to the same plant cell, or (2) a method of introducing to the same plant cell a DNA in which both of the DNAs are tandemly connected.

The presence of both of the DNAs in the transformant may be confirmed by analyzing DNA prepared from the transformant using genetic engineering analysis methods (such as confirming restriction enzyme sites, analysis of nucleotide sequence, southern hybridization, PCR and the like) described in, for example, "Molecular Cloning: A Laboratory Manual $2^{nd}$ edition" (1989), Cold Spring Harbor Laboratory Press and the like.

Specifically, for example, rice or *Arabidopsis* having introduced therein both of the DNAs can be obtained according to the method described in Model-Shokubutu-No-Jikken-Protocol: Ine, Shiroinunazuna-Hen (Supervisors: Koh SHIMAMOTO and Kiyotaka OKADA, Shujun-sha, 1996), Fourth chapter. Further, there can be obtained a soybean having introduced therein both of the DNAs by an introduction into a soybean somatic embryo with a particle gun according to the method described in Japanese Unexamined Patent Publication No. 3-291501. Likewise, a maize having introduced therein both of the DNAs can be obtained by an introduction into maize somatic embryo with a particle gun according to the method described by Fromm, M. E., et al., Bio/Technology, 8; p 838 (1990). Wheat having introduced therein both of the DNAs can be obtained by introducing the DNAs into aseptically-cultured wheat immature embryo with a particle gun according to a conventional method described by TAKUMI et al., Journal of Breeding Society (1995), 44: Extra Vol. 1, p 57. Likewise, barley having introduced therein both of the DNAs can be obtained by an introduction into aseptically-cultured barley immature embryo with a particle gun according to a conventional method described by HAGIO, et al., Journal of Breeding Society (1995), 44; Extra Vol. 1, p 67.

From thus produced transformant, a transgenic plant to which both of the DNAs have been introduced can be obtained, by regenerating a plant body according to the method for culturing the plant cell described in, for example, "Shokubutu-Saibou-Soshiki-Baiyo, Jissai, Ouyou, Tenbou", Harada, Komamine Ed., Rikogakusha (1979), p 65-118 and the like.

Further, by crossing of the transgenic plant having introduced and expressed therein both of the DNAs and a plant of the targeted variety, both of the DNAs can be introduced to a chromosome of the plant of the targeted variety, and the plant of the targeted variety to which both of the DNAs has been introduced can be obtained.

Also, by introducing separately to different plant cells, a DNA having a nucleotide sequence encoding an amino acid sequence of the protein showing PPO activity and a DNA having a nucleotide sequence encoding an amino acid sequence of the cytochrome P450 showing the present herbicidal compound metabolizing activity, and selecting and regenerating the each individual, and then crossing the progeny line of the separately regenerated transformants, the plant of the present invention can be obtained.

Specifically, for example, to produce a recombinant soybean line to which a DNA having a nucleotide sequence encoding an amino acid sequence of a variant soybean PPO (sPPOav) has been introduced and a recombinant soybean line to which a DNA having a nucleotide sequence encoding the amino acid sequence of SEQ ID NO: 1 has been introduced, both of the DNAs are separately introduced to somatic embryos of soybean by using a particle gun according to the method described in Japanese unexamined patent publication No. Hei3-291501. Next, a crossed line is obtained by crossing the produced recombinant soybean lines. For investigating the resistance of the crossed line to the present herbicidal compound, scoring evaluation may be carried out as to sensitivity in a spray test of the present herbicidal compound according to the method described below in Example 9 and the like (evaluation by scoring index based on the degree of phytotoxicity as dying of the individual and browning or whitening of the leaves or stems caused by compound spraying).

Also, concretely, for example, to produce a recombinant corn line to which a DNA having a nucleotide sequence encoding an amino acid sequence of a variant corn PPO has been introduced and a recombinant corn line to which a DNA having a nucleotide sequence encoding the amino acid sequence of SEQ ID NO: 1 has been introduced, both of the DNAs are separately introduced to somatic embryos of corn by using a particle gun according to the method described in Fromm, M. E., et al., Bio/Technology, 8; p 838 (1990). Next, a crossed line is obtained by crossing the produced recombinant corn lines. For investigating the resistance of the crossed line to the present herbicidal compound, scoring evaluation may be carried out as to sensitivity in a spray test of the present herbicidal compound according to the method described below in Example 9 and the like (evaluation by scoring index based on the degree of phytotoxicity as dying of the individual and browning or whitening of the leaves or stems caused by compound spraying).

Also, concretely, for example, to produce a recombinant cotton line to which a DNA having a nucleotide sequence encoding an amino acid sequence of a variant cotton PPO has been introduced and a recombinant cotton line to which a DNA having a nucleotide sequence encoding the amino acid sequence of SEQ ID NO: 1 has been introduced, both of the DNAs are separately introduced to cotton according to *Agrobacterium* infection method. Next, the crossed line is obtained by crossing the produced recombinant cotton lines. For investigating the resistance of the crossed line to the present herbicidal compound, scoring evaluation may be carried out as to sensitivity in a spray test of the present herbicidal compound according to the method described below in Example 9 and the like (evaluation by scoring index based on the degree of phytotoxicity as dying of the individual and browning or whitening of the leaves or stems caused by compound spraying).

Also, concretely, for example, to produce a recombinant rape line to which a DNA having a nucleotide sequence encoding an amino acid sequence of a variant rape PPO has been introduced and a recombinant rape line to which a DNA having a nucleotide sequence encoding the amino acid sequence of SEQ ID NO: 1 has been introduced, both of the DNAs are separately introduced to rape according to *Agrobacterium* infection method. Next, a crossed line is obtained by crossing produced recombinant rape lines. For investigating the resistance of the crossed line to the present herbicidal compound, scoring evaluation may be carried out as to sensitivity in a spray test of the present herbicidal compound according to the method described below in Example 9 and the like (evaluation by scoring index based on the degree of phytotoxicity as dying of the individual and browning or whitening of the leaves or stems caused by compound spraying).

Also, concretely, for example, to produce a recombinant wheat line to which a DNA having a nucleotide sequence encoding an amino acid sequence of a variant wheat PPO has been introduced and a recombinant wheat line to which a DNA having a nucleotide sequence encoding the amino acid sequence of SEQ ID NO: 1 has been introduced, both of the DNAs are separately introduced to calli derived from immature embryo of wheat by using a particle gun according to the method described in TAKUMI et al., Journal of Breeding Society (1995), 44: Extra Vol. 1, p 57. Next, a crossed line is obtained by crossing produced recombinant wheat lines. For investigating the resistance of the crossed line to the present herbicidal compound, scoring evaluation may be carried out as to sensitivity in a spray test of the present herbicidal compound according to the method described below in Example 9 and the like (evaluation by scoring index based on the degree of phytotoxicity as dying of the individual and browning or whitening of the leaves or stems caused by compound spraying).

In the method for controlling weeds of the present invention, an effective amount of the present herbicidal compound is applied to the cultivation area of the plant of the present invention. The amount of the application of the present herbicidal compound may be appropriately decided according to season of the application, variety of the weed, kind of the present herbicidal compound and the like.

The plant of the present invention may express each one kind of both of the protein showing PPO activity and the cytochrome P450 showing the present herbicidal compound metabolizing activity simultaneously, one kind of the one protein and plural kinds of the other protein simultaneously, or plural kinds of both of the proteins simultaneously. Such expression of the proteins in combination may confer synergistic resistance to the present herbicidal compound on the plant. Because degree of phytotoxicity of the plant of the present invention is highly reduced in applying the present herbicidal compound, the plant of the present invention can be grown well when the present herbicidal compound is sprayed or added to the area growing or culturing the plant of the present invention. By cultivating the plant of the present invention and applying a weed controlling agent containing the present herbicidal compound as an active ingredient to the cultivation area of the plant, it can be to remove efficiently plants such as weeds except for the plant of the present invention, then to improve the yield and quality of the plant of the present invention, to reduce the amount of application of weed controlling agents, to save the labor and the like.

EXAMPLES

Hereinafter, the present invention is further explained with Examples in detail, but not limited thereto.

Example 1

Figure 2:
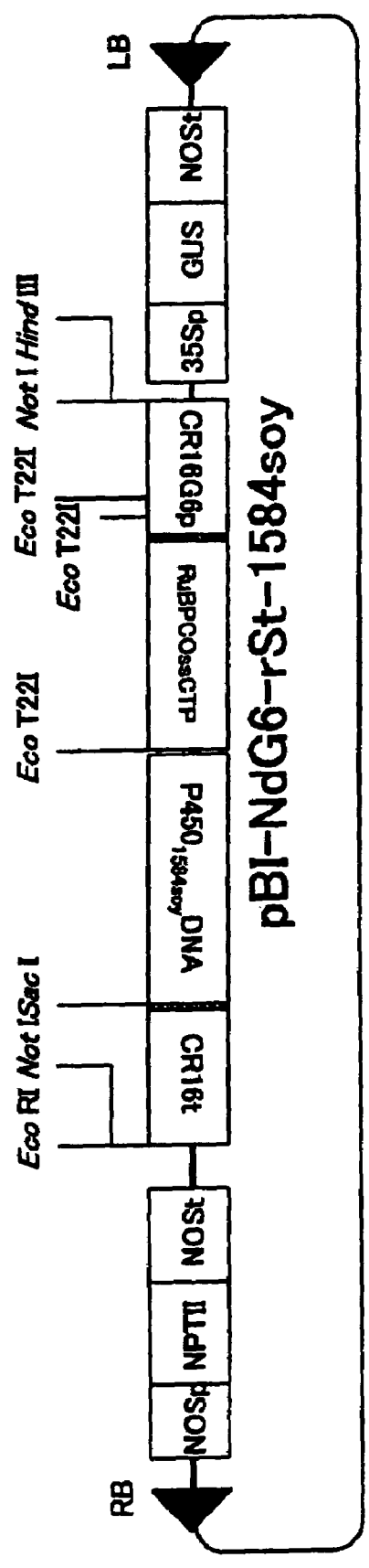
FIG. 2 shows the restriction map of the plasmid pBI-NdG6-rSt-1584soy.

Production of Recombinant Tobacco Plants into which a Cytochrome P450 Gene has been Introduced Plasmid pBI-NdG6-rSt-1609soy (FIG. 1) (described in International Patent Publication WO0304370) is a binary vector plasmid to express the chimeric protein comprising the chloroplast transit peptide sequence of soybean (cv. Jack) RuBPCO small subunit and cytochrome P450 having the amino acid sequence of SEQ ID NO: 1 under the control of CR16G6 promoter (described in International Patent Publication WO00020613). Plasmid pBI-NdG6-rSt-1584 (FIG. 2) (described in International Patent Publication WO0304370) is a binary vector plasmid to express the chimeric protein comprising the chloroplast transit peptide sequence of soybean (cv. Jack) RuBPCO small subunit and cytochrome P450 having the amino acid sequence of SEQ ID NO: 2 under the control of CR16G6 promoter (described in International Patent Publication WO00020613).

These plasmids pBI-NdG6-rSt-1609soy and pBI-NdG6-rSt-1584soy were introduced separately to *Agrobacterium tumefaciens* LBA4404 strain (manufactured by Clontech). The resultant transformants were cultured on LB agar medium (0.5% Yeast extract, 1.0% Bacto tryptone, 0.5% NaCl) containing 300 μg/L streptomycin, 100 μ/L rifampicin and 25 μ/L kanamycin, followed by selection of drug resistant colonies to isolate a recombinant *Agrobacterium* strain having plasmid pBI-NdG6-rSt-1609soy and a recombinant *Agrobacterium* strain having plasmid pBI-NdG6-rSt-1584soy respectively.

Then, according to the method described in Manual for Gene Manipulation of Plant (by Hirofumi Uchimiya, Kodansha Scientific (1992)), gene introduction to tobacco was carried out. The above recombinant *Agrobacterium* strains were each cultured at 28° C. overnight in LB liquid medium containing 300 μg/L streptomycin, 100 μ/L rifampicin and 25 μ/L kanamycin. To the obtained liquid culture medium, leaf disks sampled from aseptically-cultured tobacco (Nicotinia tabacum strain SR-1) were dipped. The leaf disks were planted on MS agar medium (MS inorganic salts, MS vitamins, 3% sucrose, and 0.8% agar; Murashige T. and Skoog F., Physiol. Plant. (1962) 15, p473) containing 0.1 mg/L naphthalene acetic acid and 1.0 mg/L benzyl aminopurine, and cultured in the light at room temperature for 2 days. Then, the leaf disks were washed with sterilized water, and cultured for 7 days on MS agar medium containing 0.1 mg/L naphthalene acetic acid, 1.0 mg/L benzyl aminopurine and 500 mg/L cefotaxime. Next, the leaf disks were transplanted to and cultured on MS agar medium containing 0.1 mg/L naphthalene acetic acid, 1.0 mg/L benzylaminopurine, 500 mg/L cefotaxime and 100 mg/L kanamycin. The culture was conducted continuously for 2 months while transplanting the leaf disks to fresh medium of the same composition at intervals of 2 weeks. During that time, the adventitious buds developed from the leaf disks were transplanted to and rooted on MS agar medium containing 100 mg/L kanamycin to obtain regenerated plants. Then, the regenerated plants were transplanted to and cultured on MS agar medium containing 100 mg/L kanamycin dispensed to culture pots (Technopot manufactured by SUMITOMO BAKELITE Co., Ltd) to obtain a recombinant tobacco individual into which the T-DNA region of plasmid pBI-NdG6-rSt-1609soy has been introduced and a recombinant tobacco individual into which the T-DNA region of plasmid pBI-NdG6-rSt-1584soy has been introduced. The obtained individuals were transplanted to growing pots containing horicultural soil (Kureha Engei Baido manufactured by Kureha Chemical Industry Co., Ltd.) from the culture pots, acclimated to the external environment in a growth chamber, then grown in a greenhouse. Flowers were covered with paper bags during flowering period to avoid crossing with other individuals, and seeds were harvested from them.

Example 2

Selection of the Recombinant Tobacco Individual with an Accumulation of the Cytochrome P450

From the recombinant tobacco individuals obtained in Example 1, recombinant tobacco individuals in which the protein having the amino acid sequence of SEQ ID NO: 1 or 2 has been accumulated in their leaves were selected by using Western blotting method. Firstly, about 1 cm square of a leaf piece of the recombinant tobacco to be assayed was sampled, and put into 2 mL sampling tube. It was added one zirconia bead of 5 mm diameter (YTZ ball manufactured by NIKKATO CORPORATION) therein and put the lid thereon, and then quickly frozen in liquid nitrogen. Using a cell disruption apparatus (Mixer Mill MM300 manufactured by QIAGEN), it was shaken twice at the rate of 30 times/second for 15 seconds to homogenize the sample. By adding 0.1 mL of sample buffer (PBS buffer (137 mM sodium chloride, 8.1 mM disodium hydrogenphosphate, 2.68 mM potassium chloride, and 1.47 mM potassium dihydrogenphosphate) containing 1 mM phenylmethylsulfonyl fluoride) and shaking, proteins were extracted. Sampling one part of the extract, the concentration of the protein in the extract was measured by using BIO-RAD Protein Assay Kit (manufactured by BIO-RAD) and measuring absorbance at 595 nm according to the protocol attached the kit using bovine serum albumin as a standard. To the extract thus prepared from the recombinant tobacco individual, it was mixed the same volume of 2×SDS sample buffer (manufactured by Nakalai tesque), heated 100° C. for 3 minutes, and then cooled on ice. It was added into the well of SDS-PAGE gel (PAG mini "Daiich" manufactured by Daiichi Pure Chemicals Co., Ltd) such that 10 μg protein was applied per 1 well. Electrophoresis was carried out in the SDS-PAGE electrophoresis buffer (tris(hydroxymethyl)aminomethane 15 g, glycine 72 g, and SDS 5 g/L) at 40 mA per gel for 1 hour. From this gel, the proteins after the electrophoresis were transferred onto PVDF membrane (Immobilon-P manufactured by Millipore) for 30 minutes at 10 V in transfer buffer of Bjerrum and Schafer-Nielsen (48 mm tris (hydroxymethyl)amino methane, 39 mM glycine, and 20% methanol) by using a semi-dry blotting device (Transblot SD cell manufactured by BIO-RAD) according to the attached instruction manual. The membrane was treated by using Immune blot kit (manufactured by BIO-RAD) and anti-rabbit IgG antibody labeled with alkaline phosphatase, and then the coloring reaction was carried out by using NBT/BCIP coloring system to detect a band of the protein extracted from the leaf of the recombinant tobacco individual. Firstly, the blocking treatment was carried out by shaking the membrane gently in TBS buffer (20 mM Tris-HCl (pH7.5) and 0.5 mM sodium chloride) containing 3% gelatin for 30 minutes at room temperature. Then, the membrane was washed with TBS buffer for 5 minutes, and gently shaken for 1 hour at room temperature with antiserum of the primary antibody diluted 3,000 fold with TBS buffer containing 0.05% Tween 20 to carry out the primary antibody reaction. As the primary antibody, the rabbit antiserum was used which was obtained by immunization of rabbit with the protein having the amino acid sequence of SEQ ID NO: 1 (described in International Patent Publication WO03040370). Next, the membrane was washed twice with TBS buffer containing 0.05% Tween 20 for 5 minutes, and then shaken gently for 1 hour at room temperature with anti-rabbit IgG antibody labeled with alkaline phosphatase (manufactured by Bio-Rad) diluted 3,000 fold with TBS buffer containing 0.05% Tween 20 to carry out the second antibody reaction. Then, the membrane was washed twice with TBS buffer containing 0.05% Tween 20 for 5 minutes and then the coloring reaction was carried out by using AP coloring kit (manufactured by Bio-Rad). The membrane after coloring was kept after drying. By the above Western blotting method, in 26 of 40 recombinant tobacco individuals to which the plasmid pBI-NdG6-rSt-1609soy containing DNA having a nucleotide sequence encoding the amino acid sequence of SEQ ID NO: 1 has been introduced, it was detected relatively high amounts of the protein having molecular weight of 44 kDa. In 6 of 20 recombinant tobacco individuals to which the plasmid pBI-NdG6-rSt-1584soy containing DNA having a nucleotide sequence encoding the amino acid sequence of SEQ ID NO: 2 has been introduced, it was detected relatively high amounts of the protein having molecular weight of 44 kDa.

These recombinant tobacco individuals in which relatively high amounts of the protein of 44 kDa was detected were selected and seeds were harvested from the selected individuals to assay copy number of the introduced gene.

Example 3

Selection of a Recombinant Tobacco Line to which 1 Copy of the Cytochrome P450 Gene has been Introduced Based on the principle that a kanamycin resistant gene and a gene connected tandem to the resistant gene are linked when these genes are introduced into a plant by *Agrobacterium* method using a binary vector, from the recombinant tobacco individuals selected in Example 2, tobacco lines in which 1 copy of the introduced gene is located on one of homologous chromosomes were further selected.

The seeds were harvested from $T_0$ generation of the recombinant tobacco individuals selected in Example 2, and dipped in a 5-fold dilution of sodium hypochlorite solution (manufactured by Nacalai tesque) for 15 minutes for sterilization. About 50 seeds treated for sterilization were aseptically seeded on MS agar medium containing 100 mg/L kanamycin, and cultured at 25° C. in the light to germinate aseptically. After about 2 weeks, germinated seedlings were observed to select tobacco lines which indicate segregation rate of 3:1 at 5% significance level by chi-square test. As the results, of 26 lines selected in Example 2 from the recombinant tobacco individuals to which the plasmid pBI-NdG6-rSt-1609soy has been introduced, 9 lines were identified and selected as lines in which 1 copy of the introduced gene is located on one of homologous chromosomes. Of 6 lines selected in Example 2 from the recombinant tobacco individuals to which the plasmid pBI-NdG6-rSt-1584soy has been introduced, 2 lines were identified and selected as lines in which 1 copy of the introduced gene is located on one of homologous chromosomes.

Next, $T_1$-generation individuals of the above selected lines were transplanted to growing pots containing horicultural soil (Kureha Engei Baido manufactured by Kureha Chemical Industry Co., Ltd.), acclimated to the external environment in a growth chamber, then grown in a greenhouse. Flowers were covered with paper bags during flowering period to avoid crossing with other individuals, and seeds were harvested from them.

Example 4

Selection of Homozygote of the Recombinant Tobacco Line to which the Cytochrome P450 Gene has been Introduced Seeds were harvested from the recombinant tobacco lines #17, #19, #22, #23, #25, #29, #30, #34 and #40 which were selected in Example 3 from among the lines to which the plasmid pBI-NdG6-rSt-1609soy has been introduced. Also, seeds were harvested from the recombinant tobacco lines #5 and #16 which were selected in Example 3 from among the lines to which the plasmid pBI-NdG6-rSt-1584soy has been introduced. Seeds of each 4 individuals of the lines #17 and #25 of the recombinant tobacco line into which the plasmid pBI-NdG6-rSt-1609soy has been introduced and the line #16 of the recombinant tobacco line to which the plasmid pBI-NdG6-rSt-1584soy has been introduced were seeded aseptically on MS agar medium containing 100 mg/L kanamycin according the method described in Example 3. An individual of which all seedlings show kanamycin resistance was selected as a homozygote.

Example 5

Production of Recombinant Tobacco Plants to which a Variant of Soybean Protoporphyrinogen IX Oxidize Gene has been Introduced DNA of a variant soybean PPO gene having a nucleotide sequence encoding the amino acid sequence of SEQ ID NO: 3 was operably linked with a promoter and a terminator which are functional in plant cells to construct an expression plasmid for expression of the variant soybean PPO gene in plant. The DNA of the variant soybean PPO gene having the nucleotide sequence encoding the amino acid sequence of SEQ ID NO: 3 was obtained by substitution of cytosine at the $677^{th}$ nucleotide of a nucleotide sequence encoding a PPO derived from soybean (*Glycine max* cv. Williams82) with thymine, whereby alanine at the $226^{th}$ amino acid residue of the PPO derived from soybean was substituted with valine.

Firstly, the plasmid pSPPO-E described in Japanese patent application publication No. Hei11-18775 was digested with restriction enzymes Sac I and Sal I to obtain a DNA having the nucleotide sequence encoding the amino acid sequence of the PPO derived from soybean between Sac I cleavage site and Sal I cleavage site (Sac I-Sal I fragment). The obtained DNA was inserted by ligation between Sac I cleavage site and Sal I cleavage site in the multicloning site of plasmid pKF18k-2 (manufactured by TAKARA BIO INC.) to subclone the DNA having the nucleotide sequence encoding the amino acid sequence of the PPO derived from soybean.

The plasmid to which the above DNA was thus subcloned was treated by using Mutan-Express Km Kit (manufactured by TAKARA BIO INC.) according to the protocol attached to the kit to substitute cytosine at the $677^{th}$ nucleotide of the nucleotide sequence encoding the amino acid sequence of the PPO derived from soybean with thymine by the Oligonucleotide-directed Dual Amber method, whereby plasmid pKF-GMP03 (FIG. 3) containing a DNA having the nucleotide sequence of SEQ ID NO: 4 between Sac I cleavage site and Sal I cleavage site in the multicloning site was obtained.

After digesting plasmid pNdG6-AT described in Example 16 of WO03040370 with restriction enzymes Bgl II and Sac I, plasmid pNdG6-#89 was constructed by inserting between the Bgl II cleavage site and the Sac I cleavage site of plasmid pNdG6-ΔT a synthetic oligonucleotide adapter containing a Sac I recognition sequence and a Sal I recognition sequence. Plasmid pNdG6-#89 contains downstream of CR16G6 promoter a Sac I recognition sequence and a Sal I recognition sequence, and thereby an expression unit to express a DNA in plant can be constructed when the DNA is inserted between cleavage sites in each of the recognition sequences. The adapter inserted in plasmid pNdG6-#89 was produced by mixing in equal volume of each 100 μM/L solution of a synthetic oligonucleotide having the nucleotide sequence 5'-GATCTGAGCTCCATGGATCCGTCGACAGCT-3' (SEQ ID NO: 13) and a synthetic oligonucleotide having the nucleotide sequence 5'-GTCGACGGATCCATG-GAGCTCA-3' (SEQ ID NO: 14), heating at 65° C. for 10 minutes, and then cooling at room temperature. Then, by digesting the above plasmid pKFGMP03 with Sac I and Sal I, it was obtained a DNA having between Sac I cleavage site and Sal I cleavage site (Sac I-Sal I fragment) the nucleotide sequence (SEQ ID NO: 4) encoding the amino acid sequence of the variant soybean PPO (SEQ ID NO: 3) in which alanine at 226$^{th}$ amino acid residue of the PPO derived from soy bean was substituted with valine (hereinafter, the variant PPO may be referred to as sPPOav). The obtained DNA was inserted by ligation between Sac I cleavage site and Sal I cleavage site of plasmid pNdG6-#89 to connect the DNA having the nucleotide sequence encoding the amino acid sequence of the variant soybean PPO (sPPOav) downstream of CR16G6 promoter. Thus, plasmid pSUM-NdG6-sPPOav (FIG. 4) containing an expression unit to express the variant soybean PPO (sPPOav) was constructed.

Next, after digesting the binary vector plasmid pBI121 (manufactured by Clontech) with restriction enzyme Not I, the DNA termini were blunted by adding nucleotides complementary to the single strand part of the resultant Not I cleavage sites, using TaKaRa BKL Kit (manufactured by TAKARA BIO INC.) according to the protocol attached to the kit. Then, the resultant DNA was self-ligated to form a plasmid.

The obtained plasmid was digested with restriction enzymes Hid III and Eco RI. Between Hind III cleavage site and Eco RI cleavage site of the digested plasmid, a DNA containing CR16G6 promoter obtained by digestion of plasmid pNdG6-ΔT with Hind III and EcoRI (Hind III II-EcoRI fragment) was inserted to construct plasmid pBI-NdG6.

Figure 5:
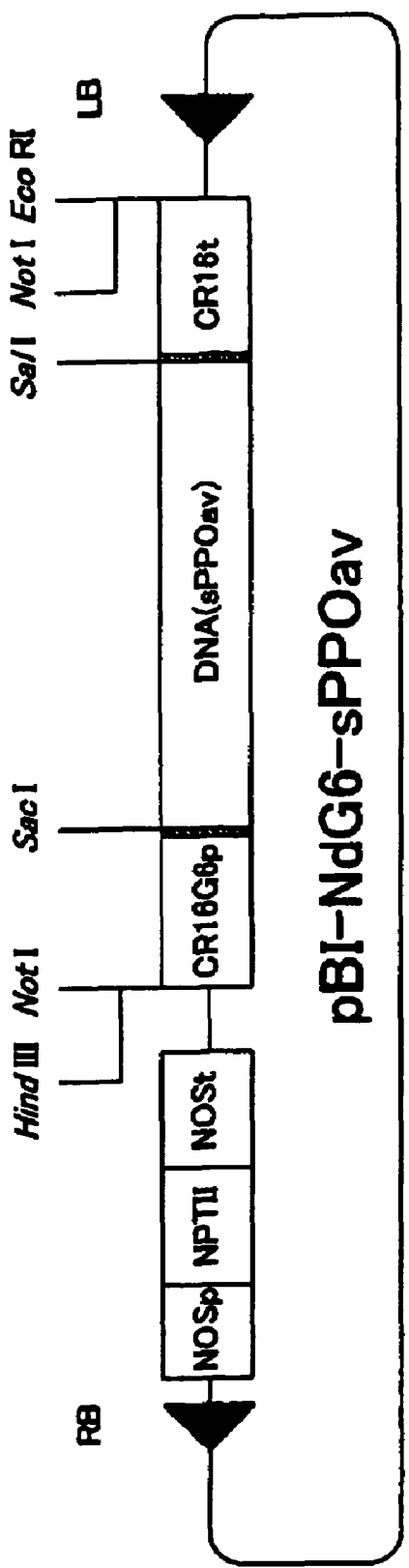
FIG. 5 shows the restriction map of the plasmid pBI-NdG6-sPPOav.

By inserting a DNA containing the expression unit obtained by digestion of plasmid pSUM-NdG6-sPPOav with Not I, to the Not I cleavage site of plasmid pBI-NdG6, plasmid pBI-NdG6-sPPOav (FIG. 5) was constructed.

By analyzing the nucleotide sequence of plasmid pBI-NdG6-sPPOav, it was confirmed that the nucleotide sequence of SEQ ID NO: 5 was contained between Hind III cleavage site and ECo RI cleavage site of the plasmid.

Figure 6:
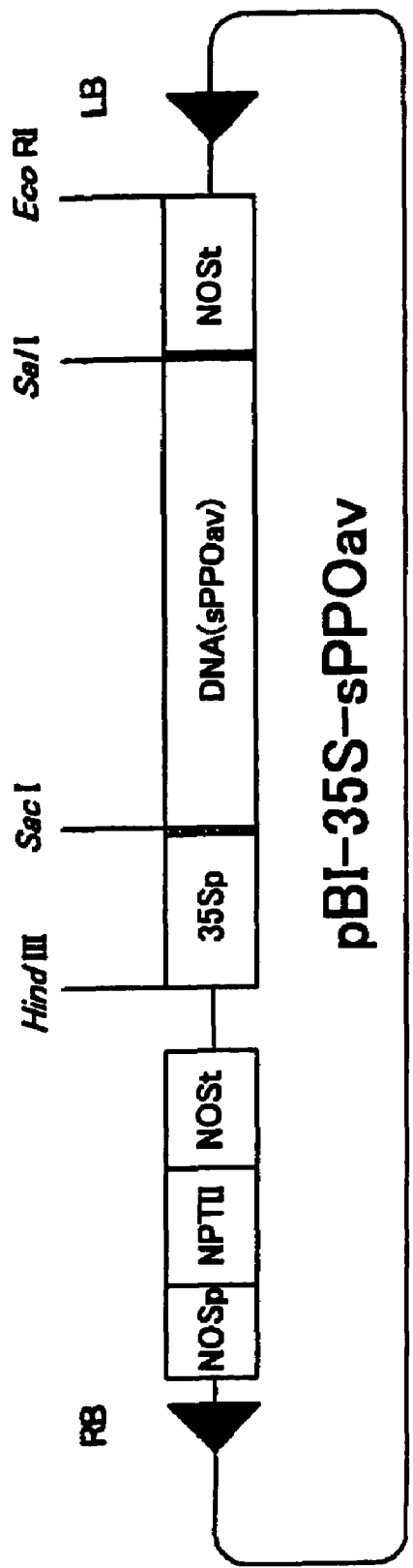
FIG. 6 shows the restriction map of the plasmid pBI-35S-sPPOav.

Next, plasmid pBI121 (manufactured by Clontech), which contains an expression unit to express an introduced gene under the control of 35S promoter derived from cauliflower mosaic virus in plant cells, was digested with restriction enzymes Bgl II and Sac I. Between Bgl II cleavage site and Sac I cleavage site of the digested plasmid pBI121, the adapter containing a Sac I recognition sequence and a Sal I recognition sequence was inserted to construct plasmid pBI121#89. Plasmid pBI121#89 contains downstream of 35S promoter a Sac I recognition sequence and a Sal I recognition sequence, and thereby an expression unit to express a DNA in plant can be constructed when the DNA is inserted between cleavage sites in each of the recognition sequences. The adapter inserted in plasmid pBI121#89 was produced by mixing in equal volume of each 100 μmol/L solution of a synthetic oligonucleotide having the nucleotide sequence 5'-GATCTGAGCTCCATGGATCCGTCGACAGCT-3' (SEQ ID NO: 13) and a synthetic oligonucleotide having the nucleotide sequence 5'-GTCGACGGATCCATG-GAGCTCA-3' (SEQ ID NO: 14), heating at 65° C. for 10 minutes, and then cooling at room temperature. Then, by digesting the above plasmid pKFGMP03 with Sac I and Sal I, it was obtained DNA having the nucleotide sequence encoding the amino acid sequence of the variant soybean PPO (sPPOav) between Sac I cleavage site and Sal I cleavage site (Sac I-Sal I fragment). The obtained DNA was inserted by ligation between Sac I cleavage site and Sal I cleavage site of plasmid pBI121#89 to connect the DNA having the nucleotide sequence encoding the amino acid sequence of the variant soybean PPO (sPPOav) downstream of 35S promoter. Thus, plasmid pBI-35S-sPPOav (FIG. 6) containing an expression unit to express the variant soybean PPO (sPPOav) was constructed.

By analyzing the nucleotide sequence of plasmid pBI-35S-sPPOav, it was confirmed that the nucleotide sequence of SEQ ID NO: 6 was contained between Hind III cleavage site and Eco RI cleavage site of the plasmid.

Thus constructed plasmid pBI-NdG6-sPPOav and plasmid pBI-35S-sPPOav were introduced separately to *Agrobacterium tumefaciens* LBA4404 strain (manufactured by Clontech) according to the method described in Example 1 such that recombinant tobacco individuals were produced by using the obtained recombinant *Agrobacterium* strains. Seeds were individually harvested from the produced recombinants.

Example 6

Selection of a Recombinant Tobacco Line to which 1 Copy of the Variant Soybean PPO (sPPOav) Gene has been Introduced From tobacco lines derived from the recombinant tobacco individuals produced in Example 5, according to the method described in Example 3, tobacco lines in which 1 copy of the introduced gene is located on one of homologous chromosomes were selected. As the results, of 27 lines of the recombinant tobacco individuals to which the plasmid pBI-NdG6-sPPOav has been introduced, 17 lines were identified and selected as lines in which 1 copy of the introduced gene is located on one of homologous chromosomes. Of 4 lines of the recombinant tobacco individuals to which the plasmid pBI-35S-sPPOav has been introduced, 3 lines were identified and selected as lines to which 1 copy of the introduced gene is located on one of homologous chromosomes.

Next, $T_1$-generation individuals of the above selected lines were transplanted to growing pots containing horicultural soil (Kureha Engei Baido manufactured by Kureha Chemical Industry Co., Ltd.), acclimated to the external environment in a growth chamber, then grown in a greenhouse. Flowers were covered with paper bags during flowering time to avoid crossing with other individuals, and seeds were from them. Using the obtained seeds, homozygotes were selected according to the method described in Example 4.

Example 7

Analysis of the Recombinant Tobacco Lines to which the Variant Soybean PPO (sPPOav) Gene has been Introduced Among the homozygotes selected in Example 6, as to the recombinant tobacco line $PO_{23}$ to which plasmid pBI-NdG6-sPPOav has been introduced and the recombinant tobacco line 35S-2 to which plasmid pBI-35S-sPPOav has been introduced, it was assayed production of the variant PPO soybean (sPPOav) by using Western blotting method according to the operations described in Example 2. As the primary antibody, it was used rat anti-soybean PPO antiserum (manufactured by ASAHI TECHNOGLASS CORPORATION), which was produced by fusing a nucleotide sequence encoding a partial peptide of the variant soybean PPO (sPPOav) downstream of dehydrofolic acid reductase gene derived from mouse (plasmid pQE-40 manufactured by QIAGEN) and expressing the fused gene to produce a fused protein, immunizing rat with the fused protein as an antigen.

By the Western blotting method, it was confirmed that the band corresponding to molecular weight of the variant soybean PPO (sPPOav) was detected from each leaf of the recombinant tobacco line P023 to which plasmid pBI-NdG6-sPPOav has been introduced and the recombinant tobacco line 35S-2 to which plasmid pBI-35S-sPPOav has been introduced.

Example 8

Crossing the Recombinant Tobacco Line in which the Variant Soybean PPO (sPPOav) Gene has been Introduced with the Recombinant Tobacco Line to which the Cytochrome P450 Gene Encoding the Amino Acid Sequence of SEQ ID NO: 1 has been Introduced It was carried out crossing the homozygote line 1609soy #25 which was selected in Example 4 from among the recombinant tobacco lines to which DNA having a nucleotide sequence encoding the amino acid sequence of SEQ ID NO: 1 (cytochrome P450) has been introduced, with the line P023 to which plasmid pBI-NdG6-sPPOav has been introduced or the line 35S-2 to which plasmid pBI-35S-sPPOav has been introduced which are homozygote lines selected in Example 6 from among the recombinant tobacco lines to which the variant soybean PPO (sPPOav) gene has been introduced. Also, it was carried out crossing the 1609soy #25 line, the P023 line or the 35S-2 line, with the wild-type tobacco strain SR-1, to produce the individuals having each introduced gene heterogeneously.

Seeds harvested from the $T_1$ generation of the recombinant tobacco individuals were aseptically seeded on MS agar medium containing 100 mg/L kanamycin. Seeds of the wild-type tobacco were aseptically seeded on MS agar medium that contains no kanamycin. Next, germinated plants were transplanted to growing pots containing horicultural soil (Kureha Engei Baido manufactured by Kureha Chemical Industry Co., Ltd.), acclimated to the external environment in a growth chamber, then grown at 23° C., 23 hours of day length in a growth chamber.

From a blossom bud of the tobacco line used as the female line, the petals were removed and the anthers before splitting were removed for emasculation. The stigma in the resultant blossom bud of the female plant was contacted with the splitting anther of the line used as the male line. Reciprocal crossing was conducted for each line. The flower after the pollination was covered with a paper bag to avoid pollination with the pollens of other lines. After the crossing, the plant was grown for about 2 months at 23° C., 23 hours of day length in a growth chamber and the seeds were collected from the flower. Seeds collected from the same pod derived from the same female plant were used as 1 line for analysis of the next generation. Name of the crossed lines thus produced, the male lines and female lines are shown in Table 1.

TABLE 1

| crossed line | female line | male line |
| --- | --- | --- |
| P-S-1 | SR-1 | P023 |
| S-P-1 | P023 | SR-1 |
| 3-S-1 | SR-1 | 35S-2 |
| S-3-1 | 35S-2 | SR-1 |
| 6-S-1 | SR-1 | 1609soy#25 |
| S-6-1 | 1609soy#25 | SR-1 |
| P-6-1 | 1609soy#25 | P023 |
| 6-P-1 | P023 | 1609soy#25 |
| 3-6-1 | 1609soy#25 | 35S-2 |
| 6-3-1 | 35S-2 | 1609soy#25 |

Example 9

Spray Test of the Present Herbicidal Compound to the Hybrid Line Between the Recombinant Tobacco Line to which the Variant Soybean PPO (sPPOav) Gene has been Introduced and the Recombinant Tobacco Line to which the Gene of the Cytochrome P450 Having the Amino Acid Sequence of SEQ ID NO: 1 has been Introduced With respect to each recombinant tobacco line produced by crossing in Example 8, seeds were aseptically seeded on MS agar medium containing 100 mg/L kanamycin. After about 2 weeks, germinated seedlings were observed. All of the crossed lines obtained by crossing using the wild-type line SR-1 as female plant showed resistance to kanamycin and grew normally.

Germinated individuals were transplanted to growing pots containing horicultural soil (Kureha Engei Baido manufactured by Kureha Chemical Industry Co., Ltd.), acclimated to the external environment in a growth chamber, then grown for about 2 weeks at 23° C., 23 hours of day length in a growth chamber. Thus obtained plants of the present invention were applied to the spray test of the present herbicidal compound.

The compound (II) of the present herbicidal compound was dissolved with Solvesso cocktail mixed Solvesso 200 (manufactured by Valent) and Sorpol 3816 (manufactured by Sumitomo Chemical Co., Ltd.) at 87.5:10 such that the compound (II) was respectively contained 0.22 mg, 0.45 mg, 0.89 mg or 1.78 mg in 0.5 mL Solvesso cocktail. The spray liquid of the present herbicidal compound was prepared as the aqueous solution containing the Solvesso cocktail of 2.5% concentration in which the compound (II) was dissolved and Agri dex of 1% concentration (manufactured by Valent) as adjuvant.

Spray of the spray liquid to the plant of the present invention above described was carried out, by using running automatic spray machine (manufactured by Nambasekkei), such that splay liquid 20 mL was sprayed to the recombinant tobacco seedlings put at 0.9 square meter of the sprayed area in a uniform way. After about 2 weeks, the sensitivity of the applied recombinant tobacco line to the compound (II) was compared to the sensitivity of wild-type tobacco line SR-1 to the compound (II). In the above spray test, 4 individuals of the recombinant tobacco were used with respect to each applied amount of the compound (II). The sensitivity of the recombinant tobacco to the compound (II) was decided by scoring it based on the later index, and calculating the average of the score of 4 individuals with respect to each recombinant tobacco 1 line and applied amount for it. And, the same spray test of wild-type line SR-1 was carried out as negative control. The results are shown in Table 2.

<Scoring Index Based on the Degree of Phytotoxicity as Dying of the Individual and Browning or Whitening of the Leaves or Stems Caused by Compound Spraying>

"0": the case in that the individual was died;
"1": the case in that phytotoxicity as browning or whitening of the leaves or stems was caused, and the phytotoxicity seriously affect the individual's growth, but it was not died;
"2": the case in that phytotoxicity as browning or whitening of the leaves or stems was caused, but the phytotoxicity did not seriously affect the individual's growth, but it was not died; and
"3": the case in that phytotoxicity as browning or whitening of the leaves or stems was small, or almost not observed.

TABLE 2

| Applied tobacco line | Applied amount of the compound (II) (mg/20 mL spray liquid) | | | |
|---|---|---|---|---|
| | 0.22 | 0.45 | 0.89 | 1.78 |
| wild type SR-1 (negative control) | 1.5 | 1.0 | 0.0 | 0.0 |
| 6-S-1 (Comparative Example) | 2.0 | 1.0 | 0.3 | 0.3 |
| S-P-1 (Comparative Example) | 3.0 | 2.0 | 2.0 | 1.5 |
| 6-P-1 (the plant of the present invention) | 3.0 | 3.0 | 2.5 | 2.5 |

Figure 7:
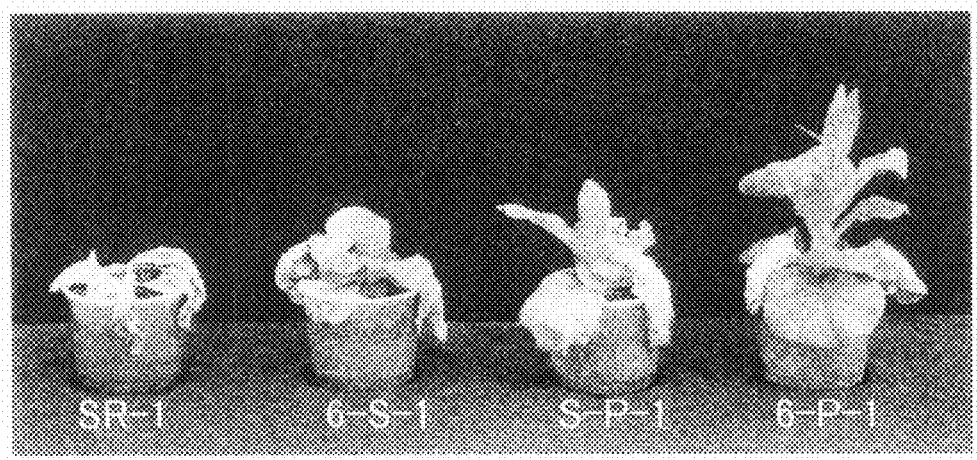
FIG. 7 shows the photos of wild-type line SR-1, the plants of comparative examples (lines 6-S-1 and S-P-1) and the present invention (line 6-P-1) grown for 14 days in a greenhouse after spraying the compound (II) (applied amount 1.78 mg/20 mL spray liquid).

And further, the photos of wild-type line SR-1, the plants of comparative examples (lines 6-S-1 and S-P-1) and the present invention (line 6-P-1) grown for 14 days in a greenhouse after spraying the compound (II) (applied amount 1.78 mg/20 mL spray liquid) are shown in FIG. 7.

Example 10

Figure 8:
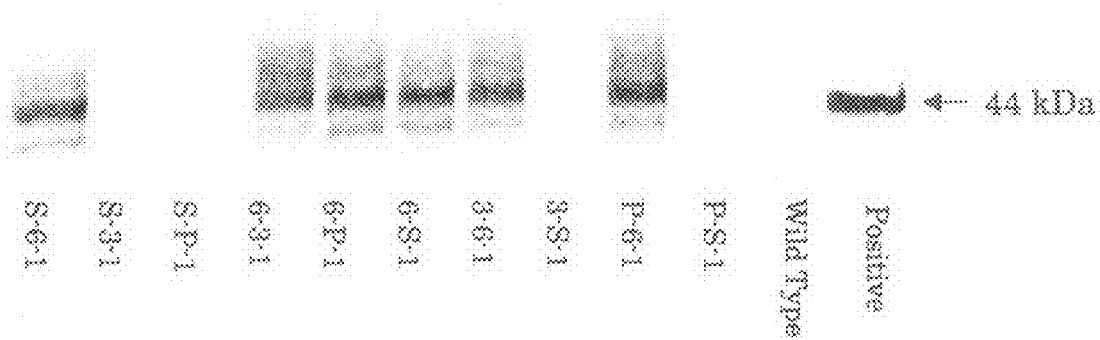
FIG. 8 is a figure indicating the results of that, before the spraying of the compound (II), as to the recombinant tobacco of lines 6-S-1, S-6-1, P-S-1, S-P-1, P-6-1, 6-P-1, 3-6-1, 6-3-1, 3-S-1 and S-3-1, expression of cytochrome P450 was assayed by using Western blotting. The protein was extracted from the leaf of each recombinant tobacco to investigate the accumulation of the protein having the amino acid sequence of SEQ ID NO: 1. The letters at bottom of the lanes in the figure indicate the line of the recombinant tobacco. Also, "Positive" indicates the results of the Western blotting followed by the electrophoresis of the 10 ng of the protein (the protein having the amino acid sequence of SEQ ID NO: 1) produced by the expression in *E. coli*, wherein said protein was the antigen to the antibody used in the above Western blotting method.

Expression Analysis of the Crossed Line Between the Recombinant Tobacco Line to which the Variant Soybean PPO (sPPOav) Gene has been Introduced and the Recombinant Tobacco Line to which the Gene of the Cytochrome P450 having the Amino Acid Sequence of SEQ ID NO: 1 has been Introduced Before the spraying of the compound (II), as to the recombinant tobacco of lines 6-S-1, S-6-1, P-S-1, S-P-1, P-6-1, 6-P-1, 3-6-1, 6-3-1, 3-S-1 and S-3-1, expression of cytochrome P450 was assayed by using Western blotting method according to the operations described in Example 2. The protein was extracted from the leaf of each recombinant tobacco to investigate the accumulation of the protein having the amino acid sequence of SEQ ID NO: 1. The results are shown in FIG. 8. In the leaves of the lines 6-S-1, S-6-1, P-6-1, 6-P-1, 3-6-1 and 6-3-1 of the recombinant tobacco, the protein of 44 kDa was detected.

Example 11

Crossing the Recombinant Tobacco Line in which the Variant Soybean PPO (sPPOav) Gene has been Introduced with the Recombinant Tobacco Line to which the Cytochrome P450 Gene Encoding the Amino Acid Sequence of SEQ ID NO: 2 has been Introduced, and Spray Test of the Present Herbicidal Compound to the Hybrid Line It was carried out the crossing the homozygote line 1584soy#16 which was selected in Example 4 from among the recombinant tobacco lines to which DNA having a nucleotide sequence encoding the amino acid sequence of SEQ ID NO: 2 has been introduced, with the line P023 to which plasmid pBI-NdG6-sPPOav has been introduced or the line 35S-2 to which plasmid pBI-35S-sPPOav has been introduced which are homozygote lines selected in Example 6 from among the recombinant tobacco lines to which the variant soybean PPO (sPPOav) gene has been introduced, according to the operations described in Example 8. Name of the produced crossed lines, the male lines and female lines are shown in Table 3.

TABLE 3

| crossed line | female line | male line |
|---|---|---|
| 5-S-1 | SR-1 | 1584soy#16 |
| S-5-1 | 1584soy#16 | SR-1 |
| P-5-1 | 1584soy#16 | P023 |
| 5-P-1 | P023 | 1584soy#16 |
| 3-5-1 | 1584soy#16 | 35S-2 |
| 5-3-1 | 35S-2 | 1584soy#16 |

Next, as to the lines SR-1, 5-S-1, S-P-1 and 5-P-1, according to the method described in Example 9 (evaluation by scoring index based on the degree of phytotoxicity as dying of the individual and browning or whitening of the leaves or stems caused by compound spraying), their sensitivities to the compound (II) were investigated. As the results, in the hybrid line 5-P-1, remarkable improvement of the resistance was recognized as compared to the line 5-S-1 or S-P-1.

Example 12

Spray Test of the Present Herbicidal Compound to the Hybrid Line Between the Recombinant Tobacco Line to which the Variant Soybean PPO (sPPOav) Gene has been Introduced and the Recombinant Tobacco Line to which the Gene of the Cytochrome P450 Having the Amino Acid Sequence of SEQ ID NO: 1 has been Introduced (ver. 2)

The tobacco individuals were obtained from the seeds of the wild-type tobacco line SR-1 and the recombinant tobacco lines 6-S-1, S-P-1 and 6-P-1 produced by crossing in Example 8, and applied to the spray test of butafenacil, flufenpyr-ethyl, the compound (III) and calfentolazonethyl, according to the operations described in Example 9. As to each herbicidal compound, (1) in the case of flufenpyr-ethyl and the compound (III), the spray liquid was prepared by dissolving each herbicidal compound separately to be contained 0.89 mg or 1.78 mg in the Solvesso cocktail 0.5 mL respectively;

(2) in the case of butafenacil, the spray liquid was prepared by dissolving the herbicidal compound to be contained 8.9 mg or 17.8 mg in the Solvesso cocktail 0.5 mL;

(3) in the case of carfentrazone-ethyl, the spray liquid was prepared by dissolving dry flowable preparation of the herbicidal compound (AIM™ HERBICIDE manufactured by FMC, containing 40% (w/w) of carfentrazone-ethyl) in Agri dex (manufactured by Valent) 1% aqueous solution to be contained 0.89 mg or 1.78 mg of the active ingredient.

Next, as to the lines SR-1, 6-S-1, S-P-1 and 6-P-1, according to the method described in Example 9 (evaluation by scoring index based on the degree of phytotoxicity as dying of the individual and browning or whitening of the leaves or stems caused by compound spraying), their sensitivities to butafenacil, flufenpyr-ethyl, the compound (III) and carfentrazone-ethyl were investigated. As the results, in the hybrid line 6-P-1, remarkable improvement of the resistance to all the herbicidal compounds was recognized as compared to the line 6-S-1 or S-P-1.

Example 13

Confirmation of Gene Introduction to Chromosome of the Hybrid Recombinant Tobacco Line It was confirmed DNA having the nucleotide sequence encoding the amino acid sequence of SEQ ID NO: 1, DNA having the nucleotide sequence encoding the amino acid sequence of SEQ ID NO: 2, or DNA having the nucleotide sequence encoding the amino acid sequence of SEQ ID NO: 3 were introduced to chromosome of the crossed recombinant tobacco line according to PCR method described hereinafter.

Figure 9:
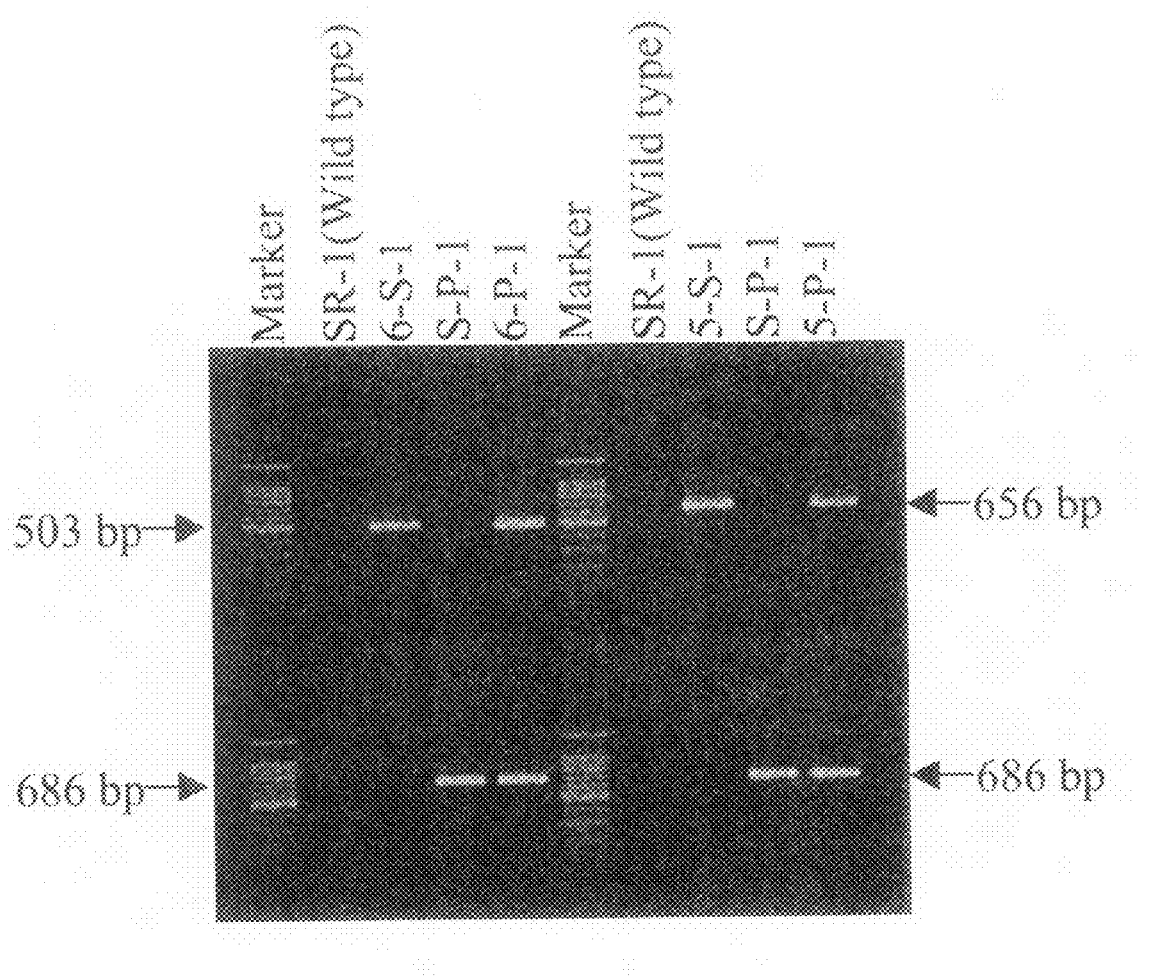
FIG. 9 is a figure indicating the results of that, as to wild-type line SR-1, the recombinant tobacco lines 6-S-1, S-P-1, 6-P-1, 5-S-1 and 5-P-1, DNAs of introduced genes were amplified from the chromosomal DNA solution by PCR, and the amplified DNAs were detected after the electrophoresis in agarose gel. "Marker" is 0.5 μg of the λ/Hind III marker (manufactured by TAKARA BIO INC.) applied to the electrophoresis.

Seeds of each of the wild-type line SR-1, the recombinant tobacco lines 6-S-1, S-P-1, 6-P-1, 5-S-1 and 5-P-1 were aseptically seeded on MS agar medium that contains no kanamycin. After sampling seedlings after 1 days from seeding, 40 µL PreMan Ultra Reagent (manufactured by Applied Biosystems) was added thereto. The obtained mixture was heated at 100° C. for 10 minutes, and then cooled. By centrifuging the cooled mixture at 15,000 rpm for 1 minute, the supernatant was obtained. The obtained supernatant was used as chromosomal DNA solution to be a template in the following PCR reaction. Using 1 µL of the chromosome DNA solution as a template, and DNA polymerase Ex-Taq-HS (manufactured by TAKARA BIO INC.), total 20 µL of the reaction mixture was prepared according to the attached protocol. The prepared reaction mixture was kept at 94° C. for 2 minutes, and repeated 30 times the cycle which was a set of the steps to keep at 94° C. for 30 seconds, then at 58° C. for 30 seconds, then at 72° C. for 1 minute, and finally kept at 72° C. for 2 minutes. As the primers, 2 kinds of the synthetic oligonucleotide in the combinations of the later (1) to (3) were used. 10 µL of the reaction mixture after the reaction was applied to the electrophoresis using an agarose gel containing 1.5% agarose in TBE buffer, and then stained the agarose gel with ethidium bromide to detect under the irradiation of 254 nm of ultraviolet a DNA amplified in the above PCR reaction. As the results, the introduced gene in chromosomal DNA was detected (FIG. 9). In the chromosome of the recombinant tobacco line 6-S-1, it was confirmed a DNA amplified in the above PCR from a DNA having a nucleotide sequence encoding the amino acid sequence of SEQ ID NO: 1. In the chromosome of the recombinant tobacco line S-P-1, it was confirmed a DNA amplified in the above PCR from a DNA having a nucleotide sequence encoding the amino acid sequence of SEQ ID NO: 3. In the chromosome of the recombinant tobacco line 6-P-1, it was confirmed DNAs amplified respectively in the above PCR from a DNA having a nucleotide sequence encoding the amino acid sequence of SEQ ID NO: 1 and from a DNA having a nucleotide sequence encoding the amino acid sequence of SEQ ID NO: 3. In the chromosome of the recombinant tobacco line 5-S-1, it was confirmed a DNA amplified in the above PCR from a DNA having a nucleotide sequence encoding the amino acid sequence of SEQ ID NO: 2. In the chromosome of the recombinant tobacco line 5-P-1, it was confirmed DNAs amplified respectively in the above PCR from a DNA having a nucleotide sequence encoding the amino acid sequence of SEQ ID NO: 2 and from a DNA having a nucleotide sequence encoding the amino acid sequence of SEQ ID NO: 3.

(1) In the Case of SEQ ID NO: 1:

It was used as primers the synthetic oligonucleotide having the nucleotide sequence of SEQ ID NO: 7, and the synthetic oligonucleotide having the nucleotide sequence of SEQ ID NO: 8. By detecting a 503 bp DNA amplified in the PCR, it was confirmed a DNA containing a nucleotide sequence encoding the amino acid sequence of SEQ ID NO: 1 was introduced.

(2) In the Case of SEQ ID NO: 2

It was used as primers the synthetic oligonucleotide having the nucleotide sequence of SEQ ID NO: 9, and the synthetic oligonucleotide having the nucleotide sequence of SEQ ID NO: 10. By detecting a 656 bp DNA amplified in the PCR, it was confirmed a DNA containing a nucleotide sequence encoding the amino acid sequence of SEQ ID NO: 2 was introduced.

(3) In the Case of SEQ ID NO: 3

It was used as primers the synthetic oligonucleotide having the nucleotide sequence of SEQ ID NO: 11, and the synthetic oligonucleotide having the nucleotide sequence of SEQ ID NO: 12. By detecting a 686 bp DNA amplified in the PCR, it was confirmed a DNA containing a nucleotide sequence encoding the amino acid sequence of SEQ ID NO: 3 was introduced.

Free Text in Sequence Listing

SEQ ID No: 4
Part of a plasmid containing a Protoporphyrinogen IX oxydase gene derived from *Glycine max*

SEQ ID No: 5
Part of an expression plasmid containing a Protoporphyrinogen IX oxydase gene derived from *Glycine max*

SEQ ID No: 6
Part of an expression plasmid containing a Protoporphyrinogen IX oxydase gene derived from *Glycine max*

SEQ ID No: 7
Designed oligonucleotide primer for PCR

SEQ ID No: 8
Designed oligonucleotide primer for PCR

SEQ ID No: 9
Designed oligonucleotide primer for PCR

SEQ ID No: 10
Designed oligonucleotide primer for PCR

SEQ ID No: 11
Designed oligonucleotide primer for PCR

SEQ ID No: 12
Designed oligonucleotide primer for PCR

SEQ ID No: 13
Designed oligonucleotide to produce an adaptor DNA

SEQ ID No: 14
Designed oligonucleotide to produce an adaptor DNA

What is claimed is:

1. A plant on which resistance to a protoporphyrinogen IX oxidase inhibitory-type herbicidal compounds is conferred, wherein to said plant both of the following DNAs have been introduced and expressed:
   (1) a DNA comprising a nucleotide sequence encoding an amino acid sequence of a protein that shows protoporphyrinogen IX oxidase activity, and
   (2) a DNA comprising a nucleotide sequence encoding an amino acid sequence of cytochrome P450 selected from the group consisting of:
      (a) cytochrome P450 having activity of metabolizing a protoporphyrinogen IX oxidase inhibitory-type herbicidal compound and comprising an amino acid sequence that has 90% or more sequence homology to the amino acid sequence of SEQ ID NO: 1 or 2,
      (b) cytochrome P450 comprising the amino acid sequence of SEQ ID NO: 1, and
      (c) cytochrome P450 comprising the amino acid sequence of SEQ ID NO: 2.

2. The plant of claim 1, wherein said protein showing protoporphyrinogen IX oxidase activity and said cytochrome P450 showing activity of metabolizing said herbicidal compound in combination in said plant results in synergistic resistance to said herbicidal compound.

3. The plant of claim 1, wherein said cytochrome P450 is cytochrome P450 derived from actinomyces.

4. The plant of claim 1, wherein said protein showing protoporphyrinogen IX oxidase activity is a protein derived from a plant and showing protoporphyrinogen IX oxidase activity.

5. The plant of claim 1, wherein said protein showing protoporphyrinogen IX oxidase activity is
   (1a) a protein derived from a plant and showing protoporphyrinogen IX oxidase activity that is inhibited by said herbicidal compound, or
   (1b) a protein derived from a plant and showing protoporphyrinogen IX oxidase activity that is not inhibited by said herbicidal compound.

6. A method for producing a herbicidal compound resistant plant comprising propagating the plant of claim 1.

7. A method for controlling weeds comprising applying to a cultivation area of the plant of claim 1, a protoporphyrinogen IX oxidase inhibitory-type herbicidal compound to which said plant exhibit resistance.

8. A method for selecting a herbicidal compound resistant plant, said method comprising:
   (1) applying or adding to a cultivation area of the plant of claim 1, a protoporphyrinogen IX oxidase inhibitory-type herbicidal compound to which said plant exhibit resistance, and
   (2) selecting a plant which has survived the weed control effect of said applied or added compound.

9. A method for conferring resistance to a protoporphyrinogen IX oxidase inhibitory-type herbicidal compounds on a plant, said method comprising introducing to and expressing in said plant both of the following DNAs:
   (1) a DNA comprising a nucleotide sequence encoding an amino acid sequence of a protein showing protoporphyrinogen IX oxidase activity, and
   (2) a DNA comprising a nucleotide sequence encoding an amino acid sequence of cytochrome P450 selected from the group consisting of:
   (a) cytochrome P450 having activity of metabolizing a protoporphyrinogen IX oxidase inhibitory-type herbicidal compound and comprising an amino acid sequence that has 90% or more sequence homology to the amino acid sequence of SEQ ID NO: 1 or 2,
   (b) cytochrome P450 comprising the amino acid sequence of SEQ ID NO: 1 and
   (c) cytochrome P450 comprising the amino acid sequence of SEQ ID NO: 2.

\* \* \* \* \*

SEQUENCE LISTING

<160> NUMBER OF SEQ ID NOS: 14

<210> SEQ ID NO 1
<211> LENGTH: 398
<212> TYPE: PRT
<213> ORGANISM: Streptomyses steffisburgensis IFO13446T

<400> SEQUENCE: 1

```
Met Ser Asp Thr Thr Ala Pro Val Ala Phe Pro Gln Ser Arg Thr Cys
 1               5                  10                  15

Pro Tyr His Pro Pro Ala Ala Tyr Glu Pro Leu Arg Ala Glu Arg Pro
                20                  25                  30

Leu Thr Arg Ile Thr Leu Phe Asp Gly Arg Glu Ala Trp Leu Val Ser
            35                  40                  45

Gly His Ala Thr Ala Arg Ala Leu Leu Ala Asp Pro Arg Leu Ser Ser
        50                  55                  60

Asp Arg Asp Arg Pro Gly Phe Pro Ala Pro Thr Ala Arg Phe Ala Gly
 65                  70                  75                  80

Ile Arg Asn Arg Arg Thr Ala Leu Leu Gly Val Asp Asp Pro Glu His
                85                  90                  95

Arg Val Gln Arg Arg Met Val Ala Gly Asp Phe Thr Leu Lys Arg Ala
               100                 105                 110

Ala Gly Leu Arg Pro Arg Ile Gln Arg Ile Val Asp Arg Arg Leu Asp
            115                 120                 125

Ala Met Ile Ala Gln Gly Pro Pro Ala Asp Leu Val Ser Ser Phe Ala
       130                 135                 140

Leu Pro Val Pro Ser Met Val Ile Cys Ala Leu Leu Gly Val Pro Tyr
145                 150                 155                 160

Ala Asp His Asp Phe Phe Glu Thr Gln Ser Arg Arg Leu Leu Arg Gly
               165                 170                 175

Pro Gln Thr Ala Asp Val Met Asp Ala Arg Ala Arg Leu Asp Glu Tyr
            180                 185                 190

Phe Gly Glu Leu Ile Asp Arg Lys Arg Lys Glu Pro Gly Ala Gly Leu
        195                 200                 205

Leu Asp Asp Leu Val Gln Arg Gln Leu Arg Asp Gly Ala Leu Asp Arg
    210                 215                 220

Glu Gly Leu Ile Ala Leu Ala Leu Ile Leu Leu Val Ala Gly His Glu
225                 230                 235                 240

Thr Thr Ala Asn Met Ile Ser Leu Gly Thr Phe Thr Leu Leu Gln His
               245                 250                 255

Pro Glu Arg Leu Ala Glu Leu Arg Ala Asp Pro Arg Leu Leu Pro Ala
            260                 265                 270

Ala Val Glu Glu Leu Met Arg Met Leu Ser Ile Ala Asp Gly Leu Leu
        275                 280                 285

Arg Leu Ala Val Glu Asp Ile Glu Val Ala Gly Thr Thr Ile Arg Lys
    290                 295                 300

Gly Asp Gly Val Val Phe Leu Thr Ser Val Ile Asn Arg Asp Glu Thr
305                 310                 315                 320

Val Tyr Pro Glu Pro Asp Thr Leu Asp Trp His Arg Ser Ala Arg His
               325                 330                 335

His Val Ala Phe Gly Phe Gly Ile His Gln Cys Leu Gly Gln Asn Leu
            340                 345                 350

Ala Arg Ala Glu Leu Glu Ile Ala Leu Trp Thr Leu Phe Asp Arg Leu
```

```
                    355                 360                 365
Pro Thr Leu Arg Leu Ala Ala Pro Ala Glu Glu Ile Ala Phe Lys Pro
    370                 375                 380

Gly Asp Thr Ile Gln Gly Met Leu Glu Leu Pro Val Thr Trp
385                 390                 395

<210> SEQ ID NO 2
<211> LENGTH: 398
<212> TYPE: PRT
<213> ORGANISM: Streptomyses roseorubens IFO13682T

<400> SEQUENCE: 2

Met Thr Asp Thr Thr Ala Pro Val Ala Phe Pro Gln Ser Arg Thr Cys
  1               5                  10                  15

Pro Tyr His Pro Pro Ala Ala Tyr Glu Pro Leu Arg Ala Glu Arg Pro
                 20                  25                  30

Leu Thr Arg Ile Thr Leu Phe Asp Gly Arg Glu Ala Trp Leu Val Ser
             35                  40                  45

Gly His Ala Thr Ala Arg Ala Leu Leu Ala Asp Pro Arg Leu Ser Ser
         50                  55                  60

Asp Arg Asp Arg Pro Gly Phe Pro Thr Pro Thr Ala Arg Phe Ala Gly
 65                  70                  75                  80

Ile Arg Asn Arg Arg Thr Ala Leu Leu Gly Val Asp Asp Pro Glu His
                 85                  90                  95

Arg Ala Gln Arg Arg Met Val Val Gly Asp Phe Thr Leu Lys Arg Ala
                100                 105                 110

Ala Ala Leu Arg Pro Arg Ile Gln Arg Ile Val Asp Glu Arg Leu Asp
            115                 120                 125

Ala Met Ile Ala Gln Gly Pro Pro Ala Asp Leu Val Ser Ala Phe Ala
        130                 135                 140

Leu Pro Val Pro Ser Met Val Ile Cys Ala Leu Leu Gly Val Pro Tyr
145                 150                 155                 160

Ala Asp His Asp Phe Phe Glu Ala Gln Ser Arg Arg Leu Leu Arg Gly
                165                 170                 175

Pro Gly Thr Ala Asp Val Gln Asp Ala Arg Ser Arg Leu Glu Glu Tyr
            180                 185                 190

Phe Gly Glu Leu Ile Asp Arg Lys Arg Glu Asp Pro Gly Thr Gly Leu
        195                 200                 205

Leu Asp Asp Leu Val Gln Arg Gln Pro Gly Asp Gly Gly Pro Asp Arg
210                 215                 220

Glu Gly Leu Ile Ala Met Ala Leu Ile Leu Leu Val Ala Gly His Glu
225                 230                 235                 240

Thr Thr Ala Asn Met Ile Ser Leu Gly Thr Phe Thr Leu Leu Gln His
                245                 250                 255

Pro Glu Arg Leu Ala Glu Leu Arg Ala Asp Ser Glu Val Met Pro Ala
            260                 265                 270

Ala Val Glu Glu Leu Met Arg Leu Leu Ser Ile Ala Asp Gly Leu Leu
        275                 280                 285

Arg Ile Ala Val Glu Asp Val Glu Val Ala Gly Thr Thr Ile Arg Ala
    290                 295                 300

Gly Glu Gly Val Val Phe Ala Thr Ser Val Ile Asn Arg Asp Glu Thr
305                 310                 315                 320

Val Phe Ala Glu Pro Asp Thr Leu Asp Trp Ser Arg Pro Ala Arg His
                325                 330                 335
```

-continued

```
His Val Ala Phe Gly Phe Gly Ile His Gln Cys Leu Gly Gln Asn Leu
            340                 345                 350

Ala Arg Ala Glu Leu Glu Ile Ala Leu Gly Thr Leu Phe Gly Arg Leu
        355                 360                 365

Pro Thr Leu Arg Leu Ala Ala Pro Pro Asp Glu Ile Pro Phe Lys Pro
    370                 375                 380

Gly Asp Thr Ile Gln Gly Met Leu Glu Leu Pro Val Thr Trp
385                 390                 395

<210> SEQ ID NO 3
<211> LENGTH: 543
<212> TYPE: PRT
<213> ORGANISM: Glycine max

<400> SEQUENCE: 3

Met Val Ser Val Phe Asn Glu Ile Leu Phe Pro Pro Asn Gln Thr Leu
  1               5                  10                  15

Leu Arg Pro Ser Leu His Ser Pro Thr Ser Phe Thr Ser Pro Thr
             20                  25                  30

Arg Lys Phe Pro Arg Ser Arg Pro Asn Pro Ile Leu Arg Cys Ser Ile
         35                  40                  45

Ala Glu Glu Ser Thr Ala Ser Pro Pro Lys Thr Arg Asp Ser Ala Pro
     50                  55                  60

Val Asp Cys Val Val Val Gly Gly Gly Val Ser Gly Leu Cys Ile Ala
 65                  70                  75                  80

Gln Ala Leu Ala Thr Lys His Ala Asn Ala Asn Val Val Thr Glu
                 85                  90                  95

Ala Arg Asp Arg Val Gly Gly Asn Ile Thr Thr Met Glu Arg Asp Gly
            100                 105                 110

Tyr Leu Trp Glu Glu Gly Pro Asn Ser Phe Gln Pro Ser Asp Pro Met
        115                 120                 125

Leu Thr Met Val Val Asp Ser Gly Leu Lys Asp Glu Leu Val Leu Gly
    130                 135                 140

Asp Pro Asp Ala Pro Arg Phe Val Leu Trp Asn Arg Lys Leu Arg Pro
145                 150                 155                 160

Val Pro Gly Lys Leu Thr Asp Leu Pro Phe Phe Asp Leu Met Ser Ile
                165                 170                 175

Gly Gly Lys Ile Arg Ala Gly Phe Gly Ala Leu Gly Ile Arg Pro Pro
            180                 185                 190

Pro Pro Gly His Glu Glu Ser Val Glu Glu Phe Val Arg Arg Asn Leu
        195                 200                 205

Gly Asp Glu Val Phe Glu Arg Leu Ile Glu Pro Phe Cys Ser Gly Val
    210                 215                 220

Tyr Val Gly Asp Pro Ser Lys Leu Ser Met Lys Ala Ala Phe Gly Lys
225                 230                 235                 240

Val Trp Lys Leu Glu Lys Asn Gly Gly Ser Ile Ile Gly Gly Thr Phe
                245                 250                 255

Lys Ala Ile Gln Glu Arg Asn Gly Ala Ser Lys Pro Pro Arg Asp Pro
            260                 265                 270

Arg Leu Pro Lys Pro Lys Gly Gln Thr Val Gly Ser Phe Arg Lys Gly
        275                 280                 285

Leu Thr Met Leu Pro Asp Ala Ile Ser Ala Arg Leu Gly Asn Lys Val
    290                 295                 300

Lys Leu Ser Trp Lys Leu Ser Ser Ile Ser Lys Leu Asp Ser Gly Glu
305                 310                 315                 320
```

```
Tyr Ser Leu Thr Tyr Glu Thr Pro Glu Gly Val Val Ser Leu Gln Cys
            325                 330                 335

Lys Thr Val Val Leu Thr Ile Pro Ser Tyr Val Ala Ser Thr Leu Leu
            340                 345                 350

Arg Pro Leu Ser Ala Ala Ala Asp Ala Leu Ser Lys Phe Tyr Tyr
            355                 360                 365

Pro Pro Val Ala Ala Val Ser Ile Ser Tyr Pro Lys Glu Ala Ile Arg
        370                 375                 380

Ser Glu Cys Leu Ile Asp Gly Glu Leu Lys Gly Phe Gly Gln Leu His
385                 390                 395                 400

Pro Arg Ser Gln Gly Val Glu Thr Leu Gly Thr Ile Tyr Ser Ser Ser
            405                 410                 415

Leu Phe Pro Asn Arg Ala Pro Pro Gly Arg Val Leu Leu Leu Asn Tyr
            420                 425                 430

Ile Gly Gly Ala Thr Asn Thr Gly Ile Leu Ser Lys Thr Asp Ser Glu
            435                 440                 445

Leu Val Glu Thr Val Asp Arg Asp Leu Arg Lys Ile Leu Ile Asn Pro
    450                 455                 460

Asn Ala Gln Asp Pro Phe Val Val Gly Val Arg Leu Trp Pro Gln Ala
465                 470                 475                 480

Ile Pro Gln Phe Leu Val Gly His Leu Asp Leu Asp Val Ala Lys
            485                 490                 495

Ala Ser Ile Arg Asn Thr Gly Phe Glu Gly Leu Phe Leu Gly Gly Asn
            500                 505                 510

Tyr Val Ser Gly Val Ala Leu Gly Arg Cys Val Glu Gly Ala Tyr Glu
            515                 520                 525

Val Ala Ala Glu Val Asn Asp Phe Leu Thr Asn Arg Val Tyr Lys
        530                 535                 540

<210> SEQ ID NO 4
<211> LENGTH: 1653
<212> TYPE: DNA
<213> ORGANISM: Artificial Sequence
<220> FEATURE:
<221> NAME/KEY: CDS
<222> LOCATION: (8)...(1639)
<220> FEATURE:
<223> OTHER INFORMATION: Part of a plasmid containing a
      Protoporphyrinogen IX oxydase gene derived from Glycine max

<400> SEQUENCE: 4 gagctcc atg gtt tcc gtc ttc aac gag atc cta ttc ccg ccg aac caa        49
        Met Val Ser Val Phe Asn Glu Ile Leu Phe Pro Pro Asn Gln
        1               5                   10 acc ctt ctt cgc ccc tcc ctc cat tcc cca acc tct ttc ttc acc tct        97
Thr Leu Leu Arg Pro Ser Leu His Ser Pro Thr Ser Phe Phe Thr Ser
15                  20                  25                  30 ccc act cga aaa ttc cct cgc tct cgc cct aac cct att cta cgc tgc       145
Pro Thr Arg Lys Phe Pro Arg Ser Arg Pro Asn Pro Ile Leu Arg Cys
                35                  40                  45 tcc att gcg gag gaa tcc acc gcg tct ccg ccc aaa acc aga gac tcc       193
Ser Ile Ala Glu Glu Ser Thr Ala Ser Pro Pro Lys Thr Arg Asp Ser
            50                  55                  60 gcc ccc gtg gac tgc gtc gtc gtc ggc gga ggc gtc agc ggc ctc tgc       241
Ala Pro Val Asp Cys Val Val Val Gly Gly Gly Val Ser Gly Leu Cys
            65                  70                  75 atc gcc cag gcc ctc gcc acc aaa cac gcc aat gcc aac gtc gtc gtc       289
Ile Ala Gln Ala Leu Ala Thr Lys His Ala Asn Ala Asn Val Val Val
```

-continued

```
                      80                  85                  90
acg gag gcc cga gac cgc gtc ggc ggc aac atc acc acg atg gag agg       337
Thr Glu Ala Arg Asp Arg Val Gly Gly Asn Ile Thr Thr Met Glu Arg
 95                 100                 105                 110 gac gga tac ctc tgg gaa gaa ggc ccc aac agc ttc cag cct tct gat       385
Asp Gly Tyr Leu Trp Glu Glu Gly Pro Asn Ser Phe Gln Pro Ser Asp
                115                 120                 125 cca atg ctc acc atg gtg gtg gac agt ggt tta aag gat gag ctt gtt       433
Pro Met Leu Thr Met Val Val Asp Ser Gly Leu Lys Asp Glu Leu Val
            130                 135                 140 ttg ggg gat cct gat gca cct cgg ttt gtg ttg tgg aac agg aag ttg       481
Leu Gly Asp Pro Asp Ala Pro Arg Phe Val Leu Trp Asn Arg Lys Leu
        145                 150                 155 agg ccg gtg ccc ggg aag ctg act gat ttg cct ttc ttt gac ttg atg       529
Arg Pro Val Pro Gly Lys Leu Thr Asp Leu Pro Phe Phe Asp Leu Met
    160                 165                 170 agc att ggt ggc aaa atc agg gct ggc ttt ggt gcg ctt gga att cgg       577
Ser Ile Gly Gly Lys Ile Arg Ala Gly Phe Gly Ala Leu Gly Ile Arg
175                 180                 185                 190 cct cct cct cca ggt cat gag gaa tcg gtt gaa gag ttt gtt cgt cgg       625
Pro Pro Pro Pro Gly His Glu Glu Ser Val Glu Glu Phe Val Arg Arg
                195                 200                 205 aac ctt ggt gat gag gtt ttt gaa cgg ttg ata gag cct ttt tgt tca       673
Asn Leu Gly Asp Glu Val Phe Glu Arg Leu Ile Glu Pro Phe Cys Ser
            210                 215                 220 ggg gtc tat gta ggc gat cct tca aaa tta agt atg aaa gca gca ttc       721
Gly Val Tyr Val Gly Asp Pro Ser Lys Leu Ser Met Lys Ala Ala Phe
        225                 230                 235 ggg aaa gtt tgg aag ctg gaa aaa aat ggt ggt agc att att ggt gga       769
Gly Lys Val Trp Lys Leu Glu Lys Asn Gly Gly Ser Ile Ile Gly Gly
    240                 245                 250 act ttc aaa gca ata caa gag aga aat gga gct tca aaa cca cct cga       817
Thr Phe Lys Ala Ile Gln Glu Arg Asn Gly Ala Ser Lys Pro Pro Arg
255                 260                 265                 270 gat ccg cgt ctg cca aaa cca aaa ggt cag act gtt gga tct ttc cgg       865
Asp Pro Arg Leu Pro Lys Pro Lys Gly Gln Thr Val Gly Ser Phe Arg
                275                 280                 285 aag gga ctt acc atg ttg cct gat gca att tct gcc aga cta ggc aac       913
Lys Gly Leu Thr Met Leu Pro Asp Ala Ile Ser Ala Arg Leu Gly Asn
            290                 295                 300 aaa gta aag tta tct tgg aag ctt tca agt att agt aaa ctg gat agt       961
Lys Val Lys Leu Ser Trp Lys Leu Ser Ser Ile Ser Lys Leu Asp Ser
        305                 310                 315 gga gag tac agt ttg aca tat gaa aca cca gaa gga gtg gtt tct ttg      1009
Gly Glu Tyr Ser Leu Thr Tyr Glu Thr Pro Glu Gly Val Val Ser Leu
    320                 325                 330 cag tgc aaa act gtt gtc ctg acc att cct tcc tat gtt gct agt aca      1057
Gln Cys Lys Thr Val Val Leu Thr Ile Pro Ser Tyr Val Ala Ser Thr
335                 340                 345                 350 ttg ctg cgt cct ctg tct gct gct gct gat gca ctt tca aag ttt          1105
Leu Leu Arg Pro Leu Ser Ala Ala Ala Asp Ala Leu Ser Lys Phe
                355                 360                 365 tat tac cct cca gtt gct gca gtt tcc ata tcc tat cca aaa gaa gct      1153
Tyr Tyr Pro Pro Val Ala Ala Val Ser Ile Ser Tyr Pro Lys Glu Ala
            370                 375                 380 att aga tca gaa tgc ttg ata gat ggt gag ttg aag ggg ttt ggt caa      1201
Ile Arg Ser Glu Cys Leu Ile Asp Gly Glu Leu Lys Gly Phe Gly Gln
        385                 390                 395 ttg cat cca cgt agc caa gga gtg gaa aca tta gga act ata tac agc      1249
Leu His Pro Arg Ser Gln Gly Val Glu Thr Leu Gly Thr Ile Tyr Ser
```

```
Leu His Pro Arg Ser Gln Gly Val Glu Thr Leu Gly Thr Ile Tyr Ser
    400                 405                 410 tca tca cta ttc ccc aac cga gca cca cct gga agg gtt cta ctc ttg      1297
Ser Ser Leu Phe Pro Asn Arg Ala Pro Pro Gly Arg Val Leu Leu Leu
415                 420                 425                 430 aat tac att gga gga gca act aat act gga att tta tcg aag acg gac      1345
Asn Tyr Ile Gly Gly Ala Thr Asn Thr Gly Ile Leu Ser Lys Thr Asp
                435                 440                 445 agt gaa ctt gtg gaa aca gtt gat cga gat ttg agg aaa atc ctt ata      1393
Ser Glu Leu Val Glu Thr Val Asp Arg Asp Leu Arg Lys Ile Leu Ile
            450                 455                 460 aac cca aat gcc cag gat cca ttt gta gtg ggg gtg aga ctg tgg cct      1441
Asn Pro Asn Ala Gln Asp Pro Phe Val Val Gly Val Arg Leu Trp Pro
        465                 470                 475 caa gct att cca cag ttc tta gtt ggc cat ctt gat ctt cta gat gtt      1489
Gln Ala Ile Pro Gln Phe Leu Val Gly His Leu Asp Leu Leu Asp Val
    480                 485                 490 gct aaa gct tct atc aga aat act ggg ttt gaa ggg ctc ttc ctt ggg      1537
Ala Lys Ala Ser Ile Arg Asn Thr Gly Phe Glu Gly Leu Phe Leu Gly
495                 500                 505                 510 ggt aat tat gtg tct ggt gtt gcc ttg gga cga tgc gtt gag gga gcc      1585
Gly Asn Tyr Val Ser Gly Val Ala Leu Gly Arg Cys Val Glu Gly Ala
                515                 520                 525 tat gag gta gca gct gaa gta aac gat ttt ctc aca aat aga gtg tac      1633
Tyr Glu Val Ala Ala Glu Val Asn Asp Phe Leu Thr Asn Arg Val Tyr
            530                 535                 540 aaa tag tagcagttgt cgac                                              1653
Lys

<210> SEQ ID NO 5
<211> LENGTH: 2930
<212> TYPE: DNA
<213> ORGANISM: Artificial Sequence
<220> FEATURE:
<221> NAME/KEY: CDS
<222> LOCATION: (930)...(2561)
<220> FEATURE:
<223> OTHER INFORMATION: Part of an expression plasmid containing a
      Protoporphyrinogen IX oxydase gene derived from Glycine max

<400> SEQUENCE: 5
aagcttgcgg ccgctatgga ttggacacgg agactaagaa aaatgtataa agtaatgtag       60
agtaaaaaga aagagaaaga aaagtgggta aagtagcggg acccatcaat atataattga      120
tagatttaga aaagtagttg aaagtagtgg gtgggtggga tttttatatt ataaaaattt      180
actattttga gaaagttttg aaatgtatag aattgagtgg gacatccata aaaggaaagt      240
gtatagaatt aaatgggaca gagggagtaa taccttatg atatataaat ttttgttatt       300
ttgatttcat aagattataa atctatgtta taatgataat ataattttaa aaataatact      360
atattaattc tgattagtcg attaccgcct tttataattt tacaatactg agtaaatgaa      420
ataaatcagt tatctgaaaa gcaaataata tctttgtaaa acagcgttcg gtcaaatggg      480
aagttcatgt gtattcaata gttttaatat aaaagtaaat tttaaattaa ttgttatttt      540
tgtttcagaa atttaaaata aattattgag catgggaagt tcacgggcat cattgagcag      600
cactagactg tttgaacaat gtatgtccgg tgtacatcta tgaccttca actcaaacta       660 gtgaataatg cattctagaa tacatctttt caaatttcaa caaacacagc tttaactttt      720
ctttcaacgg attggaatcc ttttctaaac ttttaaaat aaaaaaaatg cattattgta       780
atatttatca cacctcaac attgatgtta gcgtactata aataggtgct cttggtgctc       840
```

```
tactatcatc acatcaatct tacaccacaa accttgagct taatttttct acttattctc      900
agcaatcaca ttctaaagat ctgagctcc atg gtt tcc gtc ttc aac gag atc        953
                                Met Val Ser Val Phe Asn Glu Ile
                                 1               5 cta ttc ccg ccg aac caa acc ctt ctt cgc ccc tcc ctc cat tcc cca       1001
Leu Phe Pro Pro Asn Gln Thr Leu Leu Arg Pro Ser Leu His Ser Pro
     10              15                  20 acc tct ttc ttc acc tct ccc act cga aaa ttc cct cgc tct cgc cct       1049
Thr Ser Phe Phe Thr Ser Pro Thr Arg Lys Phe Pro Arg Ser Arg Pro
 25              30                  35                  40 aac cct att cta cgc tgc tcc att gcg gag gaa tcc acc gcg tct ccg       1097
Asn Pro Ile Leu Arg Cys Ser Ile Ala Glu Glu Ser Thr Ala Ser Pro
             45                  50                  55 ccc aaa acc aga gac tcc gcc ccc gtg gac tgc gtc gtc gtc ggc gga       1145
Pro Lys Thr Arg Asp Ser Ala Pro Val Asp Cys Val Val Val Gly Gly
         60                  65                  70 ggc gtc agc ggc ctc tgc atc gcc cag gcc ctc gcc acc aaa cac gcc       1193
Gly Val Ser Gly Leu Cys Ile Ala Gln Ala Leu Ala Thr Lys His Ala
             75                  80                  85 aat gcc aac gtc gtc gtc acg gag gcc cga gac cgc gtc ggc ggc aac       1241
Asn Ala Asn Val Val Val Thr Glu Ala Arg Asp Arg Val Gly Gly Asn
 90                  95                 100 atc acc acg atg gag agg gac gga tac ctc tgg gaa gaa ggc ccc aac       1289
Ile Thr Thr Met Glu Arg Asp Gly Tyr Leu Trp Glu Glu Gly Pro Asn
105                 110                 115                 120 agc ttc cag cct tct gat cca atg ctc acc atg gtg gtg gac agt ggt       1337
Ser Phe Gln Pro Ser Asp Pro Met Leu Thr Met Val Val Asp Ser Gly
                125                 130                 135 tta aag gat gag ctt gtt ttg ggg gat cct gat gca cct cgg ttt gtg       1385
Leu Lys Asp Glu Leu Val Leu Gly Asp Pro Asp Ala Pro Arg Phe Val
            140                 145                 150 ttg tgg aac agg aag ttg agg ccg gtg ccc ggg aag ctg act gat ttg       1433
Leu Trp Asn Arg Lys Leu Arg Pro Val Pro Gly Lys Leu Thr Asp Leu
            155                 160                 165 cct ttc ttt gac ttg atg agc att ggt ggc aaa atc agg gct ggc ttt       1481
Pro Phe Phe Asp Leu Met Ser Ile Gly Gly Lys Ile Arg Ala Gly Phe
170                 175                 180 ggt gcg ctt gga att cgg cct cct cct cca ggt cat gag gaa tcg gtt       1529
Gly Ala Leu Gly Ile Arg Pro Pro Pro Pro Gly His Glu Glu Ser Val
185                 190                 195                 200 gaa gag ttt gtt cgt cgg aac ctt ggt gat gag gtt ttt gaa cgg ttg       1577
Glu Glu Phe Val Arg Arg Asn Leu Gly Asp Glu Val Phe Glu Arg Leu
                205                 210                 215 ata gag cct ttt tgt tca ggg gtc tat gta ggc gat cct tca aaa tta       1625
Ile Glu Pro Phe Cys Ser Gly Val Tyr Val Gly Asp Pro Ser Lys Leu
            220                 225                 230 agt atg aaa gca gca ttc ggg aaa gtt tgg aag ctg gaa aaa aat ggt       1673
Ser Met Lys Ala Ala Phe Gly Lys Val Trp Lys Leu Glu Lys Asn Gly
            235                 240                 245 ggt agc att att ggt gga act ttc aaa gca ata caa gag aga aat gga       1721
Gly Ser Ile Ile Gly Gly Thr Phe Lys Ala Ile Gln Glu Arg Asn Gly
250                 255                 260 gct tca aaa cca cct cga gat ccg cgt ctg cca aaa cca aaa ggt cag       1769
Ala Ser Lys Pro Pro Arg Asp Pro Arg Leu Pro Lys Pro Lys Gly Gln
265                 270                 275                 280 act gtt gga tct ttc cgg aag gga ctt acc atg ttg cct gat gca att       1817
Thr Val Gly Ser Phe Arg Lys Gly Leu Thr Met Leu Pro Asp Ala Ile
                285                 290                 295
```

```
tct gcc aga cta ggc aac aaa gta aag tta tct tgg aag ctt tca agt    1865
Ser Ala Arg Leu Gly Asn Lys Val Lys Leu Ser Trp Lys Leu Ser Ser
            300                 305                 310 att agt aaa ctg gat agt gga gag tac agt ttg aca tat gaa aca cca    1913
Ile Ser Lys Leu Asp Ser Gly Glu Tyr Ser Leu Thr Tyr Glu Thr Pro
        315                 320                 325 gaa gga gtg gtt tct ttg cag tgc aaa act gtt gtc ctg acc att cct    1961
Glu Gly Val Val Ser Leu Gln Cys Lys Thr Val Val Leu Thr Ile Pro
    330                 335                 340 tcc tat gtt gct agt aca ttg ctg cgt cct ctg tct gct gct gct gca    2009
Ser Tyr Val Ala Ser Thr Leu Leu Arg Pro Leu Ser Ala Ala Ala Ala
345                 350                 355                 360 gat gca ctt tca aag ttt tat tac cct cca gtt gct gca gtt tcc ata    2057
Asp Ala Leu Ser Lys Phe Tyr Tyr Pro Pro Val Ala Ala Val Ser Ile
                365                 370                 375 tcc tat cca aaa gaa gct att aga tca gaa tgc ttg ata gat ggt gag    2105
Ser Tyr Pro Lys Glu Ala Ile Arg Ser Glu Cys Leu Ile Asp Gly Glu
            380                 385                 390 ttg aag ggg ttt ggt caa ttg cat cca cgt agc caa gga gtg gaa aca    2153
Leu Lys Gly Phe Gly Gln Leu His Pro Arg Ser Gln Gly Val Glu Thr
        395                 400                 405 tta gga act ata tac agc tca tca cta ttc ccc aac cga gca cca cct    2201
Leu Gly Thr Ile Tyr Ser Ser Ser Leu Phe Pro Asn Arg Ala Pro Pro
    410                 415                 420 gga agg gtt cta ctc ttg aat tac att gga gga gca act aat act gga    2249
Gly Arg Val Leu Leu Leu Asn Tyr Ile Gly Gly Ala Thr Asn Thr Gly
425                 430                 435                 440 att tta tcg aag acg gac agt gaa ctt gtg gaa aca gtt gat cga gat    2297
Ile Leu Ser Lys Thr Asp Ser Glu Leu Val Glu Thr Val Asp Arg Asp
                445                 450                 455 ttg agg aaa atc ctt ata aac cca aat gcc cag gat cca ttt gta gtg    2345
Leu Arg Lys Ile Leu Ile Asn Pro Asn Ala Gln Asp Pro Phe Val Val
            460                 465                 470 ggg gtg aga ctg tgg cct caa gct att cca cag ttc tta gtt ggc cat    2393
Gly Val Arg Leu Trp Pro Gln Ala Ile Pro Gln Phe Leu Val Gly His
        475                 480                 485 ctt gat ctt cta gat gtt gct aaa gct tct atc aga aat act ggg ttt    2441
Leu Asp Leu Leu Asp Val Ala Lys Ala Ser Ile Arg Asn Thr Gly Phe
    490                 495                 500 gaa ggg ctc ttc ctt ggg ggt aat tat gtg tct ggt gtt gcc ttg gga    2489
Glu Gly Leu Phe Leu Gly Gly Asn Tyr Val Ser Gly Val Ala Leu Gly
505                 510                 515                 520 cga tgc gtt gag gga gcc tat gag gta gca gct gaa gta aac gat ttt    2537
Arg Cys Val Glu Gly Ala Tyr Glu Val Ala Ala Glu Val Asn Asp Phe
                525                 530                 535 ctc aca aat aga gtg tac aaa tag tagcagttgt cgacagctct caacttcgta    2591
Leu Thr Asn Arg Val Tyr Lys
            540 attttatgag tgagtggagg aattgcaacg ttttcttttg tgttttgttt tcgagcaact   2651 tcataattta cagagtgagt gacagtcagt gacagaattg caactttctc tttgtacttt   2711 gttgtgactt gtgatgaata acttcatctg gctggtaatg tatgcgatct ttttaaataa   2771 aatacactat tattaaacca ataatcatat tcattctcat ttctgtgttt gtcatttctc   2831 atttagtata aacattctta taagaagtaa ctccagcttt ttgcttccac tttccttgac   2891 ccgtttgtgt aaaaaagtaa gaagtgcggc cgcgaattc                          2930

<210> SEQ ID NO 6
<211> LENGTH: 2805
```

```
<212> TYPE: DNA
<213> ORGANISM: Artificial Sequence
<220> FEATURE:
<221> NAME/KEY: CDS
<222> LOCATION: (884)...(2515)
<220> FEATURE:
<223> OTHER INFORMATION: Part of an expression plasmid containing a
      Protoporphyrinogen IX oxydase gene derived from Glycine max

<400> SEQUENCE: 6
aagcttgcat gcctgcaggt ccccagatta gccttttcaa tttcagaaag aatgctaacc     60
cacagatggt tagagaggct tacgcagcag gtctcatcaa gacgatctac ccgagcaata    120
atctccagga aatcaaatac cttcccaaga aggttaaaga tgcagtcaaa agattcagga    180
ctaactgcat caagaacaca gagaaagata tatttctcaa gatcagaagt actattccag    240
tatggacgat tcaaggcttg cttcacaaac caaggcaagt aatagagatt ggagtctcta    300
aaaaggtagt tcccactgaa tcaaaggcca tggagtcaaa gattcaaata gaggacctaa    360
cagaactcgc cgtaaagact ggcgaacagt tcatacagag tctcttacga ctcaatgaca    420
agaagaaaat cttcgtcaac atggtggagc acgacacact tgtctactcc aaaaatatca    480
aagatacagt ctcagaagac caaagggcaa ttgagacttt tcaacaaagg gtaatatccg    540
gaaacctcct cggattccat tgcccagcta tctgtcactt tattgtgaag atagtggaaa    600
aggaaggtgg ctcctacaaa tgccatcatt gcgataaagg aaaggccatc gttgaagatg    660
cctctgccga cagtggtccc aaagatggac cccacccac gaggagcatc gtggaaaaag    720
aagacgttcc aaccacgtct tcaaagcaag tggattgatg tgatatctcc actgactaa    780 gggatgacgc acaatcccac tatccttcgc aagacccttc ctctatataa ggaagttcat    840
ttcatttgga gagaacacgg gggactctag aggatcgagc tcc atg gtt tcc gtc      895
                                               Met Val Ser Val
                                                 1 ttc aac gag atc cta ttc ccg ccg aac caa acc ctt ctt cgc ccc tcc      943
Phe Asn Glu Ile Leu Phe Pro Pro Asn Gln Thr Leu Leu Arg Pro Ser
  5                  10                  15                  20 ctc cat tcc cca acc tct ttc ttc acc tct ccc act cga aaa ttc cct      991
Leu His Ser Pro Thr Ser Phe Phe Thr Ser Pro Thr Arg Lys Phe Pro
              25                  30                  35 cgc tct cgc cct aac cct att cta cgc tgc tcc att gcg gag gaa tcc     1039
Arg Ser Arg Pro Asn Pro Ile Leu Arg Cys Ser Ile Ala Glu Glu Ser
          40                  45                  50 acc gcg tct ccg ccc aaa acc aga gac tcc gcc ccc gtg gac tgc gtc     1087
Thr Ala Ser Pro Pro Lys Thr Arg Asp Ser Ala Pro Val Asp Cys Val
      55                  60                  65 gtc gtc ggc gga ggc gtc agc ggc ctc tgc atc gcc cag gcc ctc gcc     1135
Val Val Gly Gly Gly Val Ser Gly Leu Cys Ile Ala Gln Ala Leu Ala
  70                  75                  80 acc aaa cac gcc aat gcc aac gtc gtc gtc acg gag gcc cga gac cgc     1183
Thr Lys His Ala Asn Ala Asn Val Val Val Thr Glu Ala Arg Asp Arg
 85                  90                  95                 100 gtc ggc ggc aac atc acc acg atg gag agg gac gga tac ctc tgg gaa     1231
Val Gly Gly Asn Ile Thr Thr Met Glu Arg Asp Gly Tyr Leu Trp Glu
                105                 110                 115 gaa ggc ccc aac agc ttc cag cct tct gat cca atg ctc acc atg gtg     1279
Glu Gly Pro Asn Ser Phe Gln Pro Ser Asp Pro Met Leu Thr Met Val
            120                 125                 130 gtg gac agt ggt tta aag gat gag ctt gtt ttg ggg gat cct gat gca     1327
Val Asp Ser Gly Leu Lys Asp Glu Leu Val Leu Gly Asp Pro Asp Ala
        135                 140                 145
```

```
cct cgg ttt gtg ttg tgg aac agg aag ttg agg ccg gtg ccc ggg aag    1375
Pro Arg Phe Val Leu Trp Asn Arg Lys Leu Arg Pro Val Pro Gly Lys
150                 155                 160 ctg act gat ttg cct ttc ttt gac ttg atg agc att ggt ggc aaa atc    1423
Leu Thr Asp Leu Pro Phe Phe Asp Leu Met Ser Ile Gly Gly Lys Ile
165                 170                 175                 180 agg gct ggc ttt ggt gcg ctt gga att cgg cct cct cct cca ggt cat    1471
Arg Ala Gly Phe Gly Ala Leu Gly Ile Arg Pro Pro Pro Pro Gly His
                185                 190                 195 gag gaa tcg gtt gaa gag ttt gtt cgt cgg aac ctt ggt gat gag gtt    1519
Glu Glu Ser Val Glu Glu Phe Val Arg Arg Asn Leu Gly Asp Glu Val
            200                 205                 210 ttt gaa cgg ttg ata gag cct ttt tgt tca ggg gtc tat gta ggc gat    1567
Phe Glu Arg Leu Ile Glu Pro Phe Cys Ser Gly Val Tyr Val Gly Asp
        215                 220                 225 cct tca aaa tta agt atg aaa gca gca ttc ggg aaa gtt tgg aag ctg    1615
Pro Ser Lys Leu Ser Met Lys Ala Ala Phe Gly Lys Val Trp Lys Leu
    230                 235                 240 gaa aaa aat ggt ggt agc att att ggt gga act ttc aaa gca ata caa    1663
Glu Lys Asn Gly Gly Ser Ile Ile Gly Gly Thr Phe Lys Ala Ile Gln
245                 250                 255                 260 gag aga aat gga gct tca aaa cca cct cga gat ccg cgt ctg cca aaa    1711
Glu Arg Asn Gly Ala Ser Lys Pro Pro Arg Asp Pro Arg Leu Pro Lys
                265                 270                 275 cca aaa ggt cag act gtt gga tct ttc cgg aag gga ctt acc atg ttg    1759
Pro Lys Gly Gln Thr Val Gly Ser Phe Arg Lys Gly Leu Thr Met Leu
            280                 285                 290 cct gat gca att tct gcc aga cta ggc aac aaa gta aag tta tct tgg    1807
Pro Asp Ala Ile Ser Ala Arg Leu Gly Asn Lys Val Lys Leu Ser Trp
        295                 300                 305 aag ctt tca agt att agt aaa ctg gat agt gga gag tac agt ttg aca    1855
Lys Leu Ser Ser Ile Ser Lys Leu Asp Ser Gly Glu Tyr Ser Leu Thr
    310                 315                 320 tat gaa aca cca gaa gga gtg gtt tct ttg cag tgc aaa act gtt gtc    1903
Tyr Glu Thr Pro Glu Gly Val Val Ser Leu Gln Cys Lys Thr Val Val
325                 330                 335                 340 ctg acc att cct tcc tat gtt gct agt aca ttg ctg cgt cct ctg tct    1951
Leu Thr Ile Pro Ser Tyr Val Ala Ser Thr Leu Leu Arg Pro Leu Ser
                345                 350                 355 gct gct gct gca gat gca ctt tca aag ttt tat tac cct cca gtt gct    1999
Ala Ala Ala Ala Asp Ala Leu Ser Lys Phe Tyr Tyr Pro Pro Val Ala
            360                 365                 370 gca gtt tcc ata tcc tat cca aaa gaa gct att aga tca gaa tgc ttg    2047
Ala Val Ser Ile Ser Tyr Pro Lys Glu Ala Ile Arg Ser Glu Cys Leu
        375                 380                 385 ata gat ggt gag ttg aag ggg ttt ggt caa ttg cat cca cgt agc caa    2095
Ile Asp Gly Glu Leu Lys Gly Phe Gly Gln Leu His Pro Arg Ser Gln
    390                 395                 400 gga gtg gaa aca tta gga act ata tac agc tca tca cta ttc ccc aac    2143
Gly Val Glu Thr Leu Gly Thr Ile Tyr Ser Ser Ser Leu Phe Pro Asn
405                 410                 415                 420 cga gca cca cct gga agg gtt cta ctc ttg aat tac att gga gga gca    2191
Arg Ala Pro Pro Gly Arg Val Leu Leu Leu Asn Tyr Ile Gly Gly Ala
                425                 430                 435 act aat act gga att tta tcg aag acg gac agt gaa ctt gtg gaa aca    2239
Thr Asn Thr Gly Ile Leu Ser Lys Thr Asp Ser Glu Leu Val Glu Thr
            440                 445                 450 gtt gat cga gat ttg agg aaa atc ctt ata aac cca aat gcc cag gat    2287
Val Asp Arg Asp Leu Arg Lys Ile Leu Ile Asn Pro Asn Ala Gln Asp
        455                 460                 465
```

```
cca ttt gta gtg ggg gtg aga ctg tgg cct caa gct att cca cag ttc    2335
Pro Phe Val Val Gly Val Arg Leu Trp Pro Gln Ala Ile Pro Gln Phe
    470                 475                 480 tta gtt ggc cat ctt gat ctt cta gat gtt gct aaa gct tct atc aga    2383
Leu Val Gly His Leu Asp Leu Leu Asp Val Ala Lys Ala Ser Ile Arg
485                 490                 495                 500 aat act ggg ttt gaa ggg ctc ttc ctt ggg ggt aat tat gtg tct ggt    2431
Asn Thr Gly Phe Glu Gly Leu Phe Leu Gly Gly Asn Tyr Val Ser Gly
                505                 510                 515 gtt gcc ttg gga cga tgc gtt gag gga gcc tat gag gta gca gct gaa    2479
Val Ala Leu Gly Arg Cys Val Glu Gly Ala Tyr Glu Val Ala Ala Glu
            520                 525                 530 gta aac gat ttt ctc aca aat aga gtg tac aaa tag tagcagttgt cgacag  2531
Val Asn Asp Phe Leu Thr Asn Arg Val Tyr Lys
        535                 540 ctcgaatttc ccgatcgtt caaacatttg gcaataaagt ttcttaagat tgaatcctgt   2591
tgccggtctt gcgatgatta tcatataatt tctgttgaat tacgttaagc atgtaataat  2651
taacatgtaa tgcatgacgt tatttatgag atgggttttt atgattagag tcccgcaatt  2711
atacatttaa tacgcgatag aaaacaaaat atagcgcgca aactaggata aattatcgcg  2771
cgcggtgtca tctatgttac tagatcggga attc                              2805

<210> SEQ ID NO 7
<211> LENGTH: 25
<212> TYPE: DNA
<213> ORGANISM: Artificial Sequence
<220> FEATURE:
<223> OTHER INFORMATION: Designed oligonucleotide primer for PCR

<400> SEQUENCE: 7
aggctttcat ctgatcgtga cagac                                         25

<210> SEQ ID NO 8
<211> LENGTH: 25
<212> TYPE: DNA
<213> ORGANISM: Artificial Sequence
<220> FEATURE:
<223> OTHER INFORMATION: Designed oligonucleotide primer for PCR

<400> SEQUENCE: 8
atcagacctt ccctgtctaa tgctc                                         25

<210> SEQ ID NO 9
<211> LENGTH: 25
<212> TYPE: DNA
<213> ORGANISM: Artificial Sequence
<220> FEATURE:
<223> OTHER INFORMATION: Designed oligonucleotide primer for PCR

<400> SEQUENCE: 9
gctttgctag gtgttcccta tgctg                                         25

<210> SEQ ID NO 10
<211> LENGTH: 25
<212> TYPE: DNA
<213> ORGANISM: Artificial Sequence
<220> FEATURE:
<223> OTHER INFORMATION: Designed oligonucleotide primer for PCR

<400> SEQUENCE: 10
ctaagtgtgg gcaacctacc gaaga                                         25
```

```
<210> SEQ ID NO 11
<211> LENGTH: 18
<212> TYPE: DNA
<213> ORGANISM: Artificial Sequence
<220> FEATURE:
<223> OTHER INFORMATION: Designed oligonucleotide primer for PCR

<400> SEQUENCE: 11
ttgttcaggg gtctatgt                                                18

<210> SEQ ID NO 12
<211> LENGTH: 18
<212> TYPE: DNA
<213> ORGANISM: Artificial Sequence
<220> FEATURE:
<223> OTHER INFORMATION: Designed oligonucleotide primer for PCR

<400> SEQUENCE: 12
gttcactgtc cgtcttcg                                                18

<210> SEQ ID NO 13
<211> LENGTH: 30
<212> TYPE: DNA
<213> ORGANISM: Artificial Sequence
<220> FEATURE:
<223> OTHER INFORMATION: Designed oligonucleotide to produce an adaptor
      DNA

<400> SEQUENCE: 13
gatctgagct ccatggatcc gtcgacagct                                   30

<210> SEQ ID NO 14
<211> LENGTH: 22
<212> TYPE: DNA
<213> ORGANISM: Artificial Sequence
<220> FEATURE:
<223> OTHER INFORMATION: Designed oligonucleotide to produce an adaptor
      DNA

<400> SEQUENCE: 14
gtcgacggat ccatggagct ca                                           22
```